(12) United States Patent
Saragovi et al.

(10) Patent No.: US 10,363,305 B2
(45) Date of Patent: Jul. 30, 2019

(54) ANTI-GANGLIOSIDE COMPOUND FOR TARGETING CANCER AND GENERATING ANTIBODIES

(71) Applicant: REALIST PHARMA, INC., Toronto (CA)

(72) Inventors: Horacio Uri Saragovi, Montreal (CA); Wenyong Tong, San Diego, CA (US)

(73) Assignee: Horacio Url Saragovi, Montreal QC (CA)

( * ) Notice: Subject to any disclaimer, the term of this patent is extended or adjusted under 35 U.S.C. 154(b) by 0 days.

(21) Appl. No.: 15/101,428

(22) PCT Filed: Dec. 4, 2014

(86) PCT No.: PCT/CA2014/051165
§ 371 (c)(1),
(2) Date: Jun. 3, 2016

(87) PCT Pub. No.: WO2015/081438
PCT Pub. Date: Jun. 11, 2015

(65) Prior Publication Data
US 2016/0303227 A1    Oct. 20, 2016

Related U.S. Application Data

(60) Provisional application No. 61/912,684, filed on Dec. 6, 2013.

(51) Int. Cl.
| | | |
|---|---|---|
| *A61K 39/00* | (2006.01) | |
| *A61K 39/385* | (2006.01) | |
| *C07H 15/203* | (2006.01) | |
| *C07K 16/30* | (2006.01) | |
| *C07K 16/44* | (2006.01) | |

(52) U.S. Cl.
CPC ........ *A61K 39/385* (2013.01); *A61K 39/0011* (2013.01); *C07H 15/203* (2013.01); *C07K 16/3084* (2013.01); *C07K 16/44* (2013.01); *A61K 2039/575* (2013.01); *A61K 2039/645* (2013.01); *A61K 2039/70* (2013.01); *C07K 2317/21* (2013.01); *C07K 2317/24* (2013.01); *C07K 2317/73* (2013.01); *C07K 2317/76* (2013.01)

(58) Field of Classification Search
None
See application file for complete search history.

(56) References Cited

FOREIGN PATENT DOCUMENTS

| | | | |
|---|---|---|---|
| JP | 2003073397 A | 3/2003 | |
| JP | 2004518704 A | 6/2004 | |
| JP | 2006-347908 A | 12/2006 | |
| JP | 2008031156 A | 2/2008 | |
| WO | WO-9416731 A1 * | 8/1994 | ............ A63K 31/70 |
| WO | WO2004041310 A1 | 5/2004 | |
| WO | WO03003985 A2 | 7/2017 | |

OTHER PUBLICATIONS

Helling, ANN N Y Acad Sci, Aug. 12, 1993;690:396-7.*
Hollinger et al., "Synthesis of mucin O-glycan core structures as their p-nitro- and p-aminophenyl glycosides," Carbohydr Res. 346(12):1454-66 (2011) (14 pages).
Zeng et al., "Effective chemoenzymatic synthesis of p-aminophenyl glycosides of sialyl N-acetyllactosaminide and analysis of their interactions with lectins," Carbohydr Res. 342(9):1244-8 (2007) (7 pages).
International Search Report of PCT/CA2014/051165.
Thompson et al., "Oligosaccharide-derivatized dendrimers: Defined multivalent inhibitors of the adherence of the cholera toxin B subunit and the heat labile enterotoxin of *E. coli* to GM1," Glycoconj J. 14(7):837-845 (1997).
Zhang et al., "Antibodies against GD2 ganglioside can eradicate syngeneic cancer micrometastases," Cancer Res. 58(13):2844-2849 (1998).
European Search Report for European Patent Application No. 14868142.2, dated Jul. 12, 2017 (9 pages).
Yoshimi Murozuka et al., "Lyso-GM3, its dimer, and multimer: their synthesis, and their effect on epidermal growth actor-induced receptor tyrosine kinase", Glycoconjugate Journal, Klewer academic publishers, BO, vol. 24, No. 9, Jul. 19, 2007, pp. 551-563.
Qiu Et al., "Combining sybthetis carbohydrate vaccines with cancer cell glycoengineering for effective cancer immunotherapy", Cance Immunol, Immunothe, Nov. 2012, 61(11), 1-17.
Astronomo et al, "Carbohydrate vaccines, developing sweet solutions to stickysituations?", Nat Rev Drug Discov., Apr. 2010, 9(4), 1-32.

* cited by examiner

*Primary Examiner* — Layla D Berry
(74) *Attorney, Agent, or Firm* — Norton Rose Fulbright Canada LLP

(57) ABSTRACT

It is provided a multivalent ganglioside carbohydrate as a therapeutic cancer vaccine. The GD2 and GD3 carbohydrate conjugated disclosed are linked by a spacer to form a multimer which conserves the native structural feature of naturally occurring GD2 or GD3, the tetramer being immunogenic and elicits cytotoxic anti-gangliosides humoral and cellular responses in vivo.

11 Claims, 15 Drawing Sheets

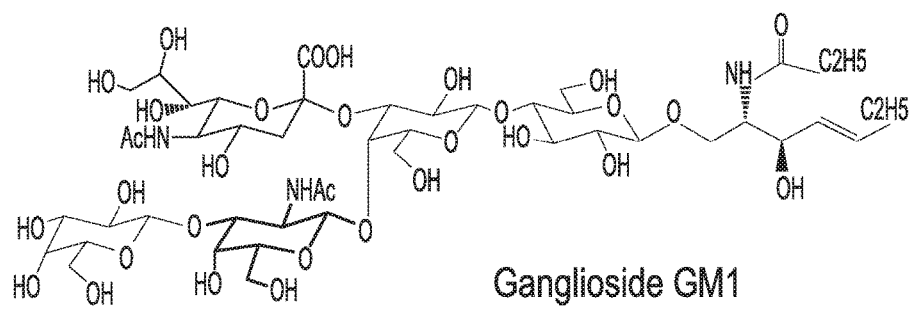
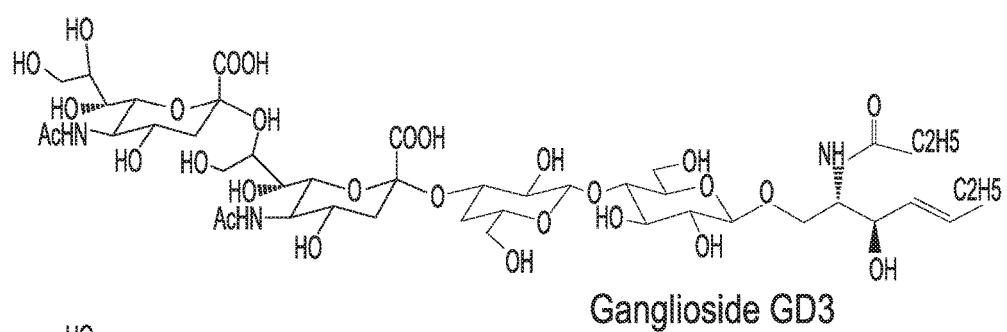
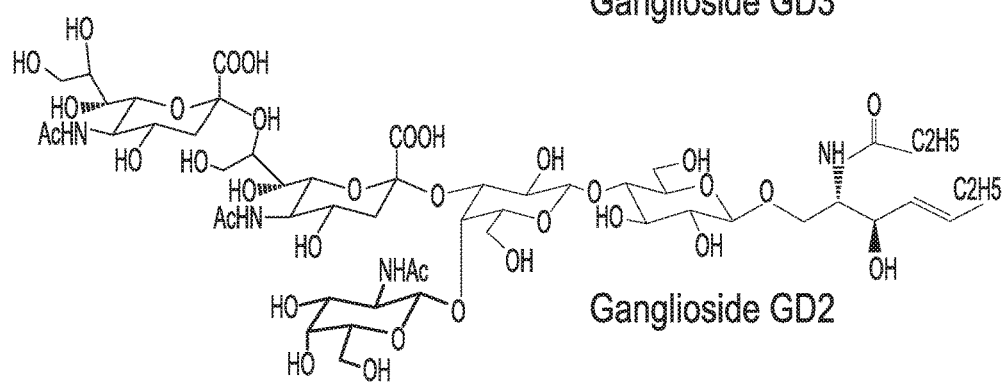
FIG. 1A

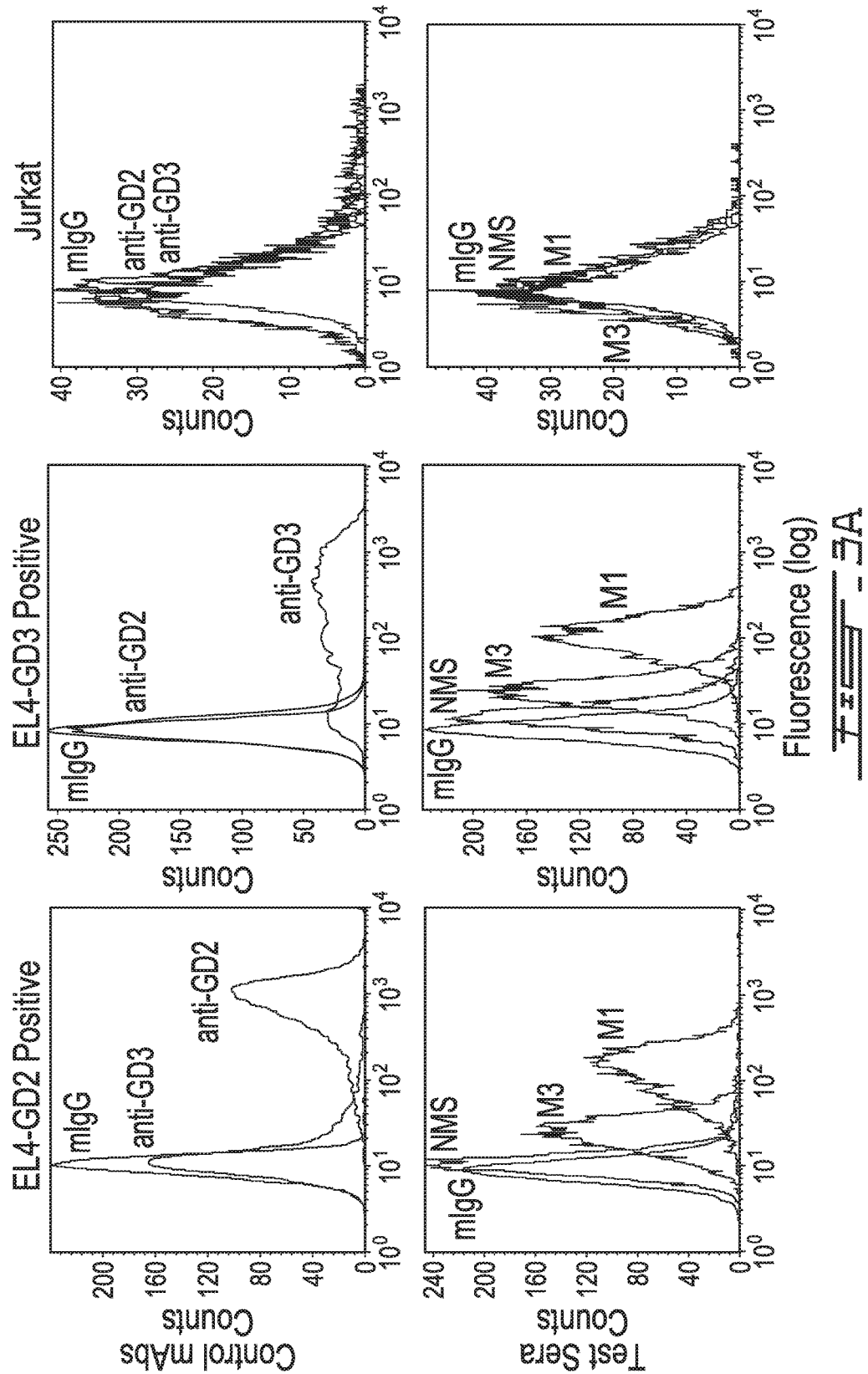

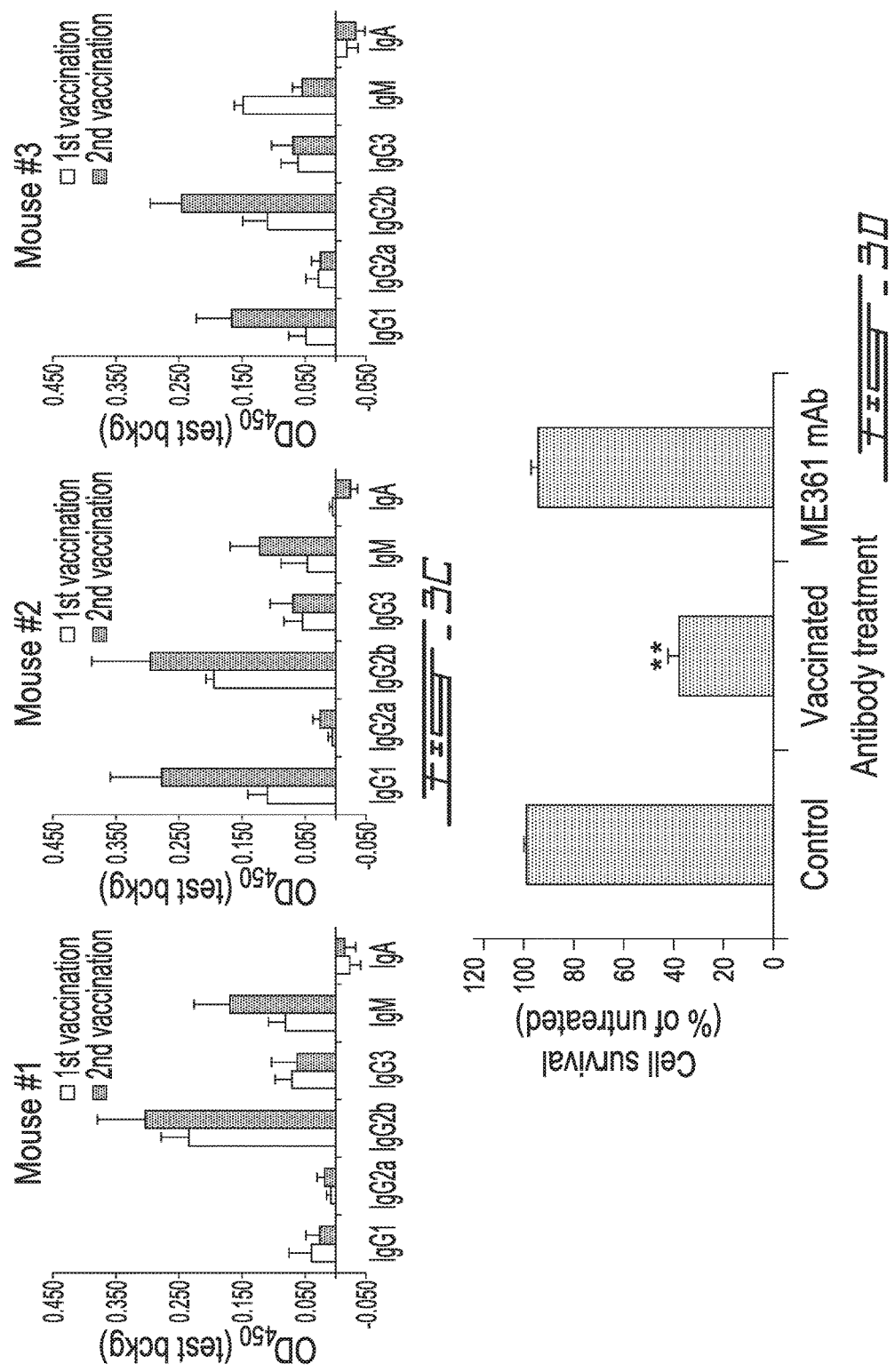

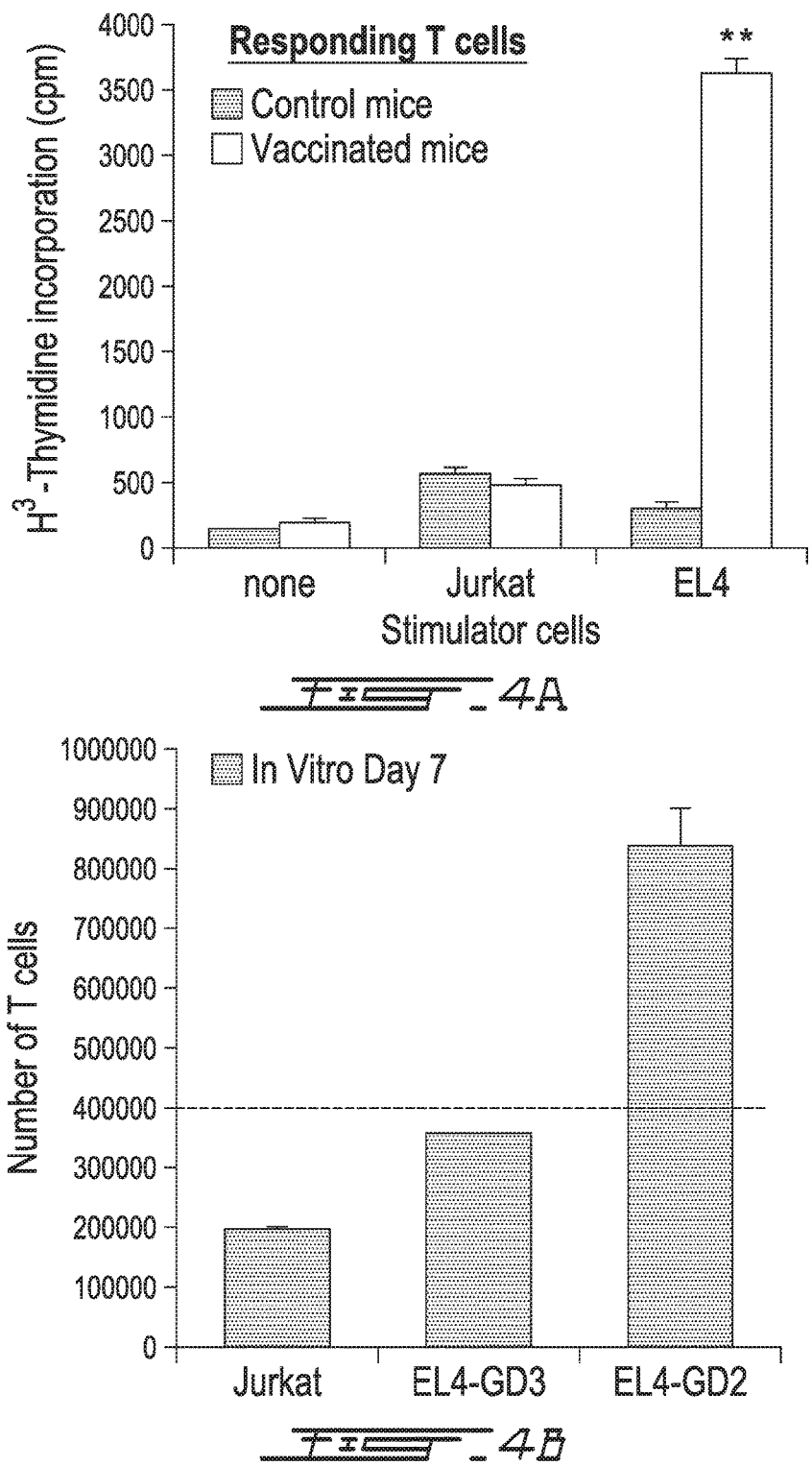

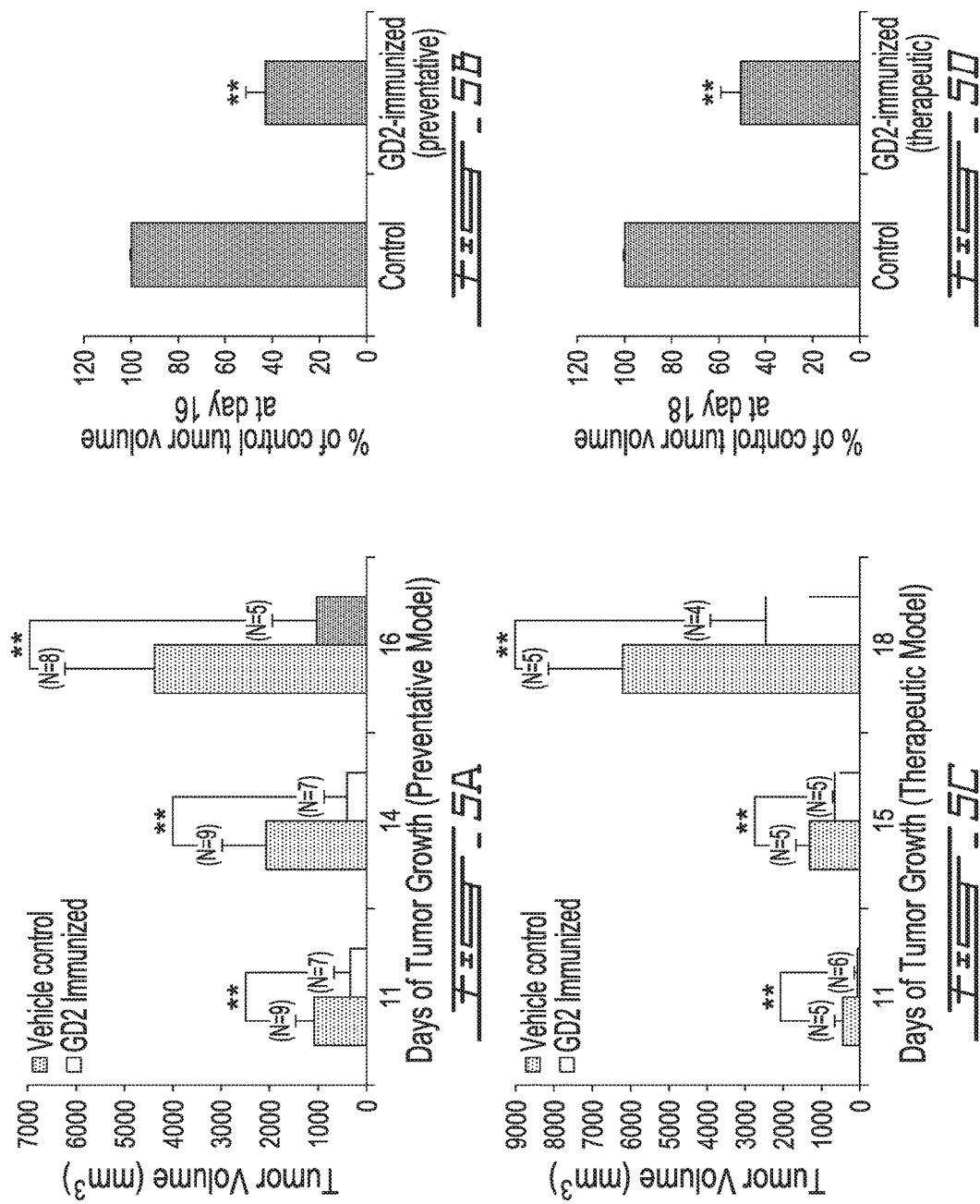

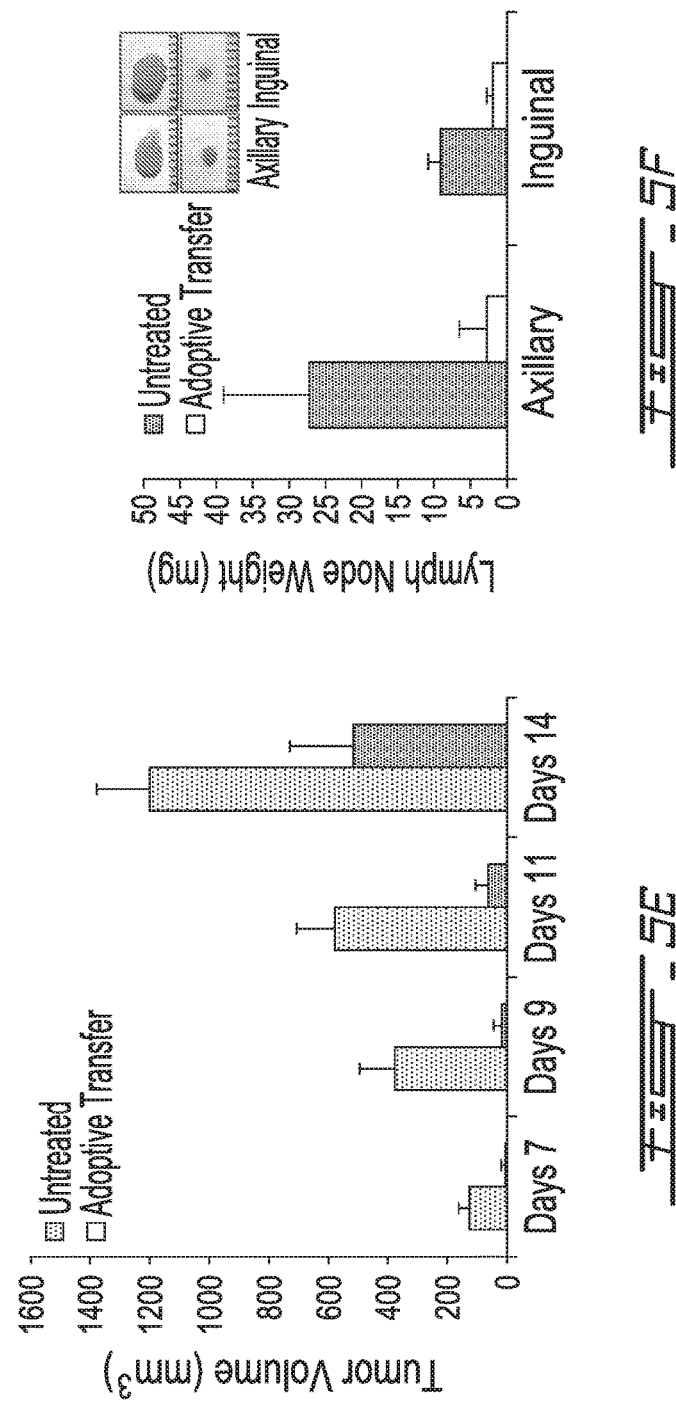

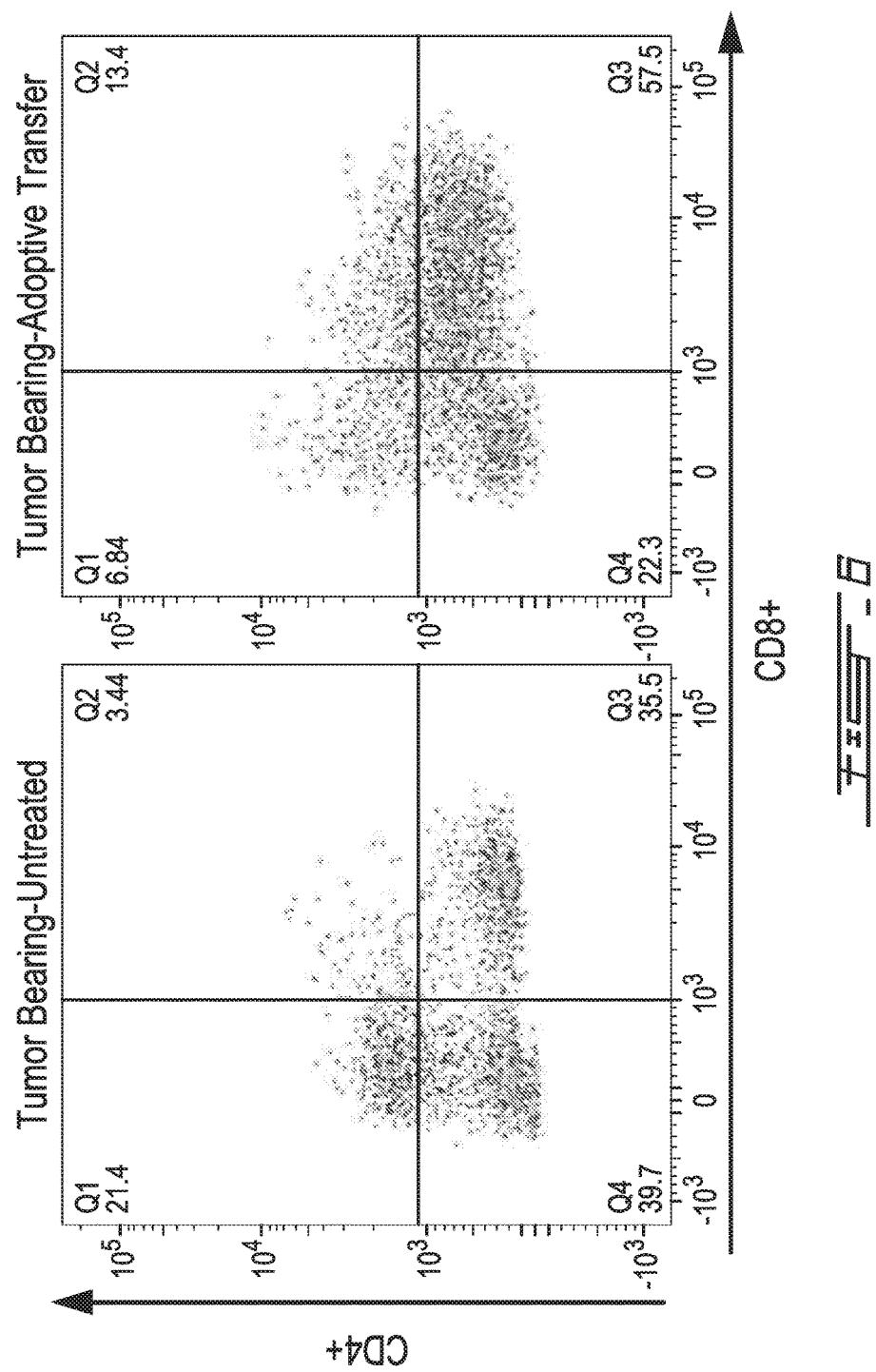

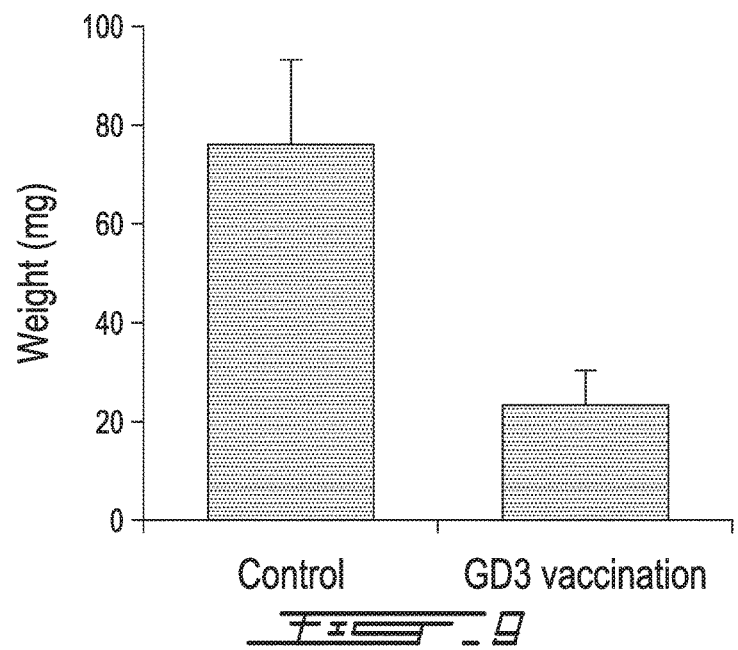
FIG. 9
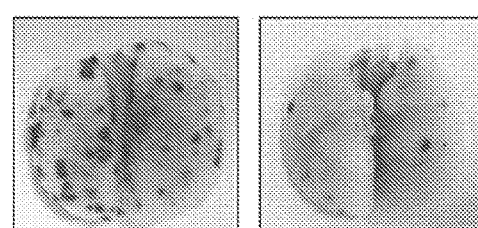
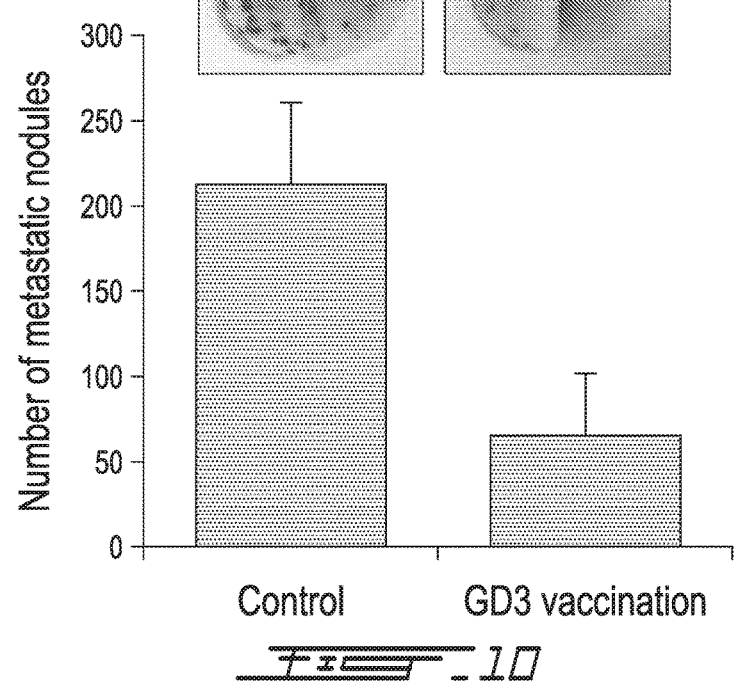
FIG. 10

ANTI-GANGLIOSIDE COMPOUND FOR TARGETING CANCER AND GENERATING ANTIBODIES

REFERENCE TO CROSS-RELATED APPLICATION

This application claims priority on PCT/CA2014/051165 filed Dec. 4, 2014, which itself claimed priority on U.S. provisional application Ser. 61/912,684, filed Dec. 6, 2013, the entire content of these applications being incorporated herein by reference in their entirety.

TECHNICAL FIELD

The present description relates to ganglioside glycoconjugates and use thereof as anti-tumor vaccines.

BACKGROUND ART

Gangliosides are neuraminic acid-containing glycosphingolipids that accumulate in the outer leaflet of plasma membranes. Gangliosides such as GD2 and GD3 are prevalent tumor markers. They are expressed in neuroblastoma, melanoma, small cell lung cancer and gliomas (Hakomori, 1996, Cancer Research, 56: 5309) as well as breast cancer stem cells (Battula et al., 2012, The Journal of clinical investigations, 122: 2066), but they are absent in normal cells. Hence, GD2 and GD3 have been exploited as tumor targets, and they are validated clinical targets. Partial therapy can be achieved by passively administering purified anti-GD2 (Cheung et al., 1987, J Clin Oncol, 5: 1430) or anti-GD3 monoclonal antibodies (mAbs) (Houghton et al., 1985, Proc Natl Acad Sci USA, 82: 1242). However, passive immunity has high financial cost, significant side effects, limited frequency of intervention, and low therapeutic efficacy (Navid et al., 2010, Current Cancer Drug Targets, 10: 200).

As an alternative, many groups have pursued active immunotherapy gangliosides (Astronomo and Burton, 2010, Nat Rev Drug Discov, 9: 308). However, serious difficulties associated with gangliosides include poor immunogenicity, poor solubility and poor formulations, limited access and difficulty to prepare well-characterized and homogeneous immunogens, and the potential of poor selectivity with the risk of cross-reactivity to non-tumor gangliosides that are highly related in structure.

For example, a GD2 lactone chemically conjugated to keyhole limpet hemocyanin (KLH) is immunogenic, and can induce antibodies that delay tumor growth in mice (Chapman et al., 2000, Clinical Cancer Research, 6: 4658). The antibodies induced by this vaccine act through a complement-dependent cytotoxicity (CDC) mechanism (Kim et al., 2011, Cancer Immunology, Immunotherapy, 60: 621). However, the KLH-ganglioside conjugation yields chemically heterogeneous products (Danieshefsky and Allen, 2000, Angew Chem Int Ed, 39: 836), which is a serious drawback. Other ganglioside conjugates have shown poor immunogenicity and generally elicited a low and transient anti-ganglioside antibody response (Ragupathi et al., 2000, International Journal of Cancer, 85: 659). Even the most immunogenic ganglioside, a GM2-KLH vaccine did not provide clinical benefits (Kirkwood et al., 2001, Journal of Clinical Oncology, 19: 2370) and was discontinued. Additional experimental approaches include GD2-peptide mimotopes (Wondimu et al., 2008, Cancer Immunology, Immunotherapy, 57: 1079), GD2-mimicking peptides (Bolesta et al., 2005, Cancer Research, 65: 3410), and GD2 mimotope DNA vaccines (Zeytin et al., 2000, Cancer Gene Therapy, 7: 1426) that can induce cross-reactive immunity to GD2. However, immune responses were not very effective at protecting the host in tumor-therapy paradigms (Bleeke et al., 2009, European Journal of Cancer, 45: 2915).

There is thus still a need to be provided with a new therapeutic approach using gangliosides as targets.

SUMMARY

In accordance with one aspect, there is provided a ganglioside carbohydrate of the formula: G-Aryl-NH2 wherein G is an oligosaccharide comprising one or more sialic acids (e.g. n-acetylneuraminic acid), wherein said G is covalently bonded to the aryl by the C1 anomeric oxygen atom, and G is immunogenic, and Aryl is a C6 to C10 aryl, optionally substituted.

The ganglioside carbohydrate provided herein is immunogenic against tumours. More particularly, it is provided a ganglioside carbohydrate immunogenic against tumours for preventing or treating cancer.

In accordance with the present description, there also provided a ganglioside carbohydrate multimer comprising at least one or at least two carbohydrate ganglioside analogues or ganglioside carbohydrate as described herein covalently bonded to a multimeric core molecule There is provided an antibody specifically binding to the ganglioside carbohydrate or the ganglioside carbohydrate multimer as defined herein.

There is also provided a vaccine comprising the ganglioside carbohydrate or the ganglioside carbohydrate multimer as defined herein.

There is also provided the use of the ganglioside carbohydrate or the ganglioside carbohydrate multimer as defined herein for preventing or treating cancer.

There is also provided the use of the ganglioside carbohydrate or the ganglioside carbohydrate multimer as defined herein in the manufacture of a medicament for preventing or treating cancer.

There is also provided a method of preventing or treating cancer in a patient in need thereof comprising the step of administering to said patient an effective amount of the ganglioside carbohydrate or the ganglioside carbohydrate multimer as defined herein.

There is also provided a method of eliciting an immunogenic response in a patient in need thereof comprising the step of administering to said patient an effective amount of the ganglioside carbohydrate or the ganglioside carbohydrate multimer as defined herein.

There is also provided a pharmaceutical composition comprising an effective amount of the ganglioside carbohydrate multimer as defined herein and a pharmaceutically suitable carrier or excipient.

BRIEF DESCRIPTION OF THE DRAWINGS

Reference will now be made to the accompanying drawings, in which:

FIG. 1A illustrates the structure of gangliosides GM1, GD3 and GD2.

(AP-GD2) in deuterated water.

FIG. 3A illustrates a representative FACScan data showing the presence of anti-GD2-reactive antibodies of the IgG class; FIG. 3C illustrates isotyping of the sera showing the increase of IgG and IgM isotypes after each round of immunization; FIG. 3D illustrates EL4-GD2+ cells growing exponentially in complete media cultured with the indicated antibodies and their survival/metabolism quantified by MTT after 24 hours;

FIG. 4A illustrates T cell proliferation evaluated by $^3$H-thymidine incorporation assays, wherein tumor cells were cultured at a 1:10 ratio with T cells purified from vaccinated or from naïve mice; FIG. 4B illustrates GD2-dependent T cell proliferation measured by Trypan Blue exclusion;

FIG. 5A illustrates measured tumor volume of mice vaccinated intraperitoneally; FIG. 5B illustrates average tumor volumes measured for immunized versus control mice; FIG. 5C illustrates tumor volume measured in mice vaccinated intraperitoneally with tetra-GD2; FIG. 5D illustrates average tumor volumes for immunized versus control mice; FIG. 5E illustrates adoptive transfer therapy effect; FIG. 5F illustrates the quantification of metastasis to the lymph nodes;

FIG. 6 illustrates purified T cells from 2 groups of tumor-bearing mice naïve (control or vaccinated), and CD4/CD8 profiles of the cells quantified by FACScan;

FIGS. 8 and 9 represent the results of vaccination with tetra-GD3; and

FIG. 10 illustrates the count of metastatic nodules after vaccination using the GD3 vaccine.

DETAILED DESCRIPTION

Figure 1B:
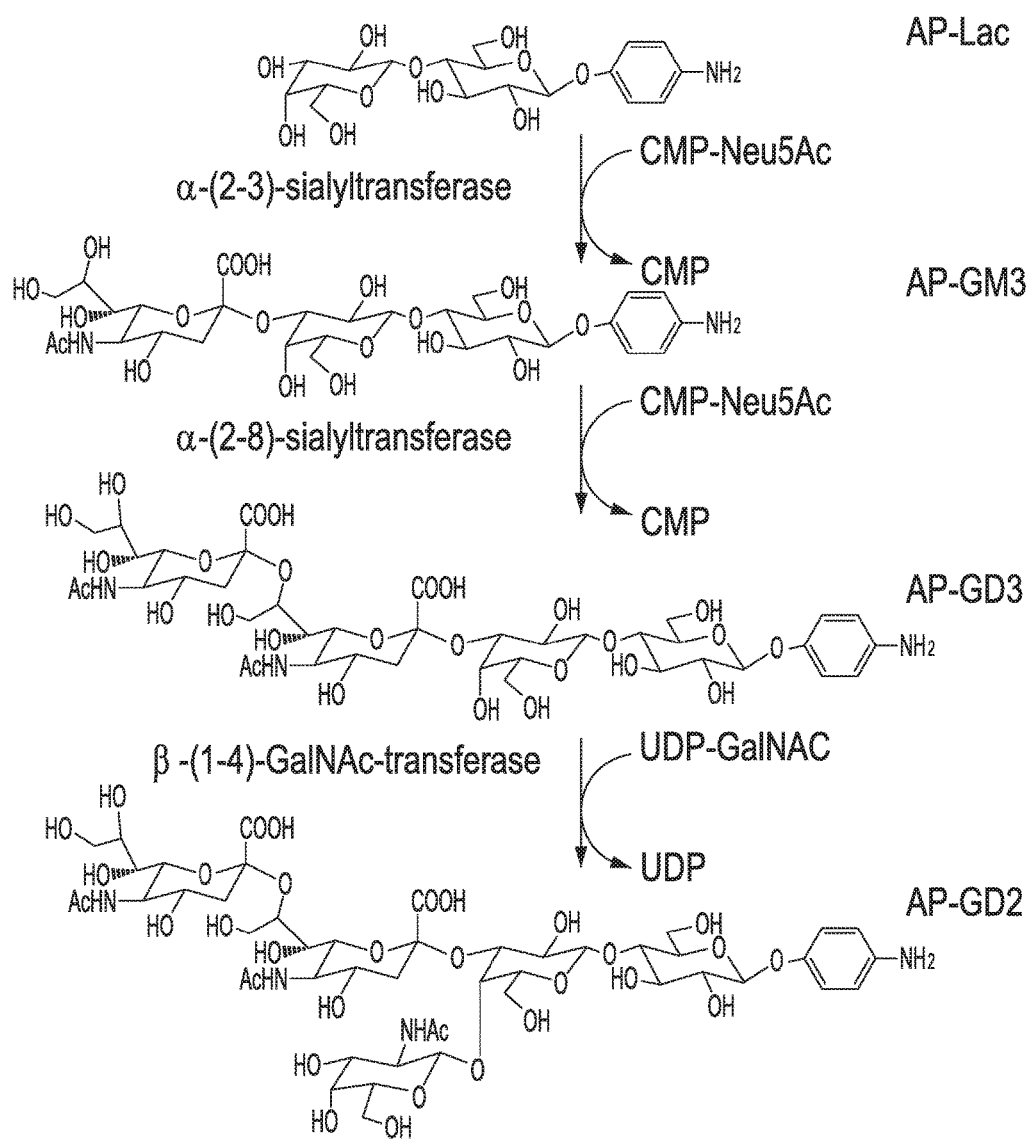
FIG. 1B illustrates a scheme for the synthesis of GD2 and GD3 analogs as disclosed herein.

The present disclosure relates to a ganglioside carbohydrate consisting of

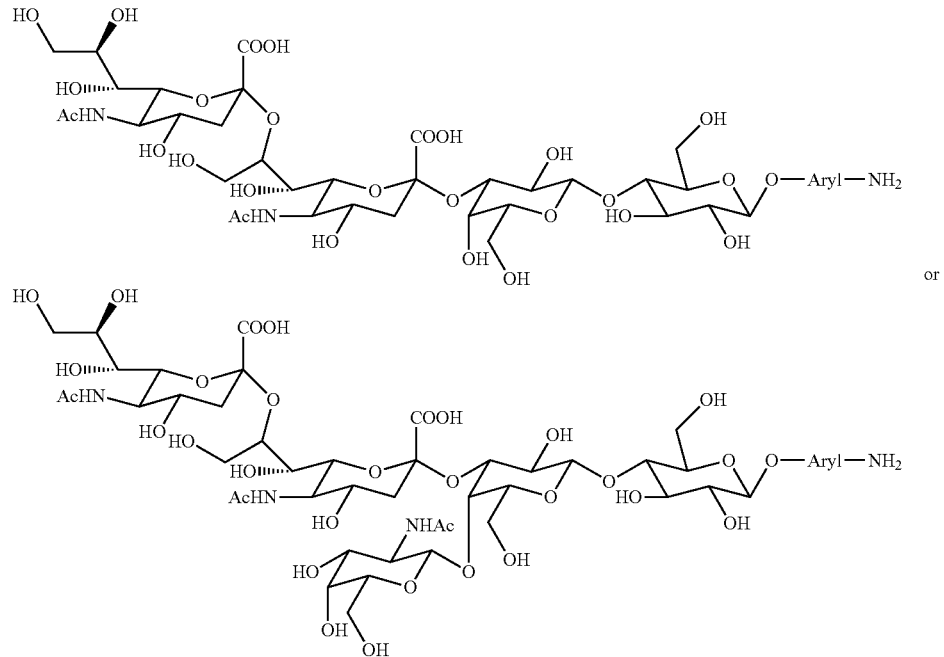

The present disclosure specifically provides a ganglioside carbohydrate consisting of

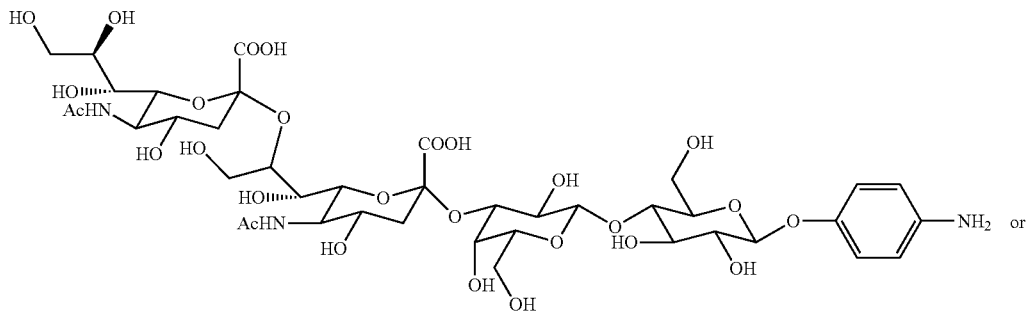

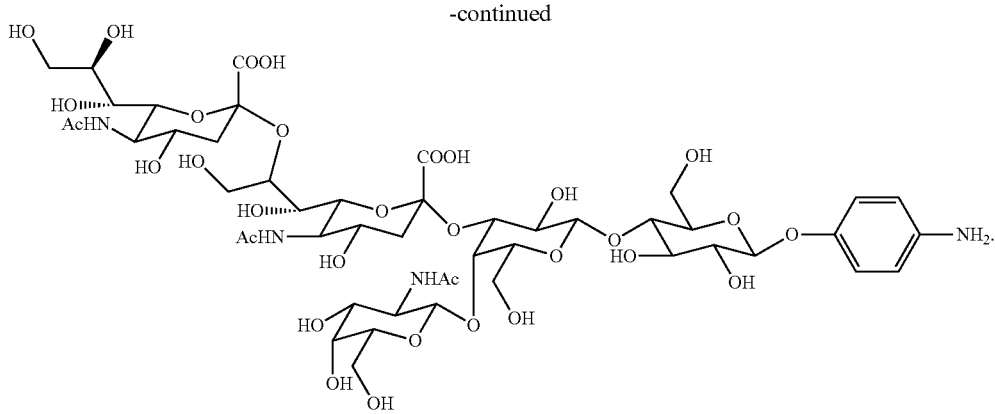

As used herein, G refers to part of the respective ganglioside (such as GD2, GD3, GM2 and GT1b) comprising only the oligosaccharide and sialic acids (e.g. n-acetyl-neuraminic acid, NANA), and corresponding to the respective ganglioside. Stated differently, G refers to the oligosaccharide and sialic acids of the corresponding ganglioside, excluding the ceramide portion of the ganglioside which is herein replaced by an amino-aryl residue (such as an aminophenyl). Examples of G as used herein include the residues of GD3 and GD2 such as The term "optionally substituted" with regard to the aryl means optionally substituted with one or more of an alkyl, aryl, or halogen, at any available position or positions. Preferably, there is no substituent.

The present disclosure provides a ganglioside carbohydrate multimer comprising at least one or at least two carbohydrate ganglioside analogues covalently bonded to a multimeric core molecule.

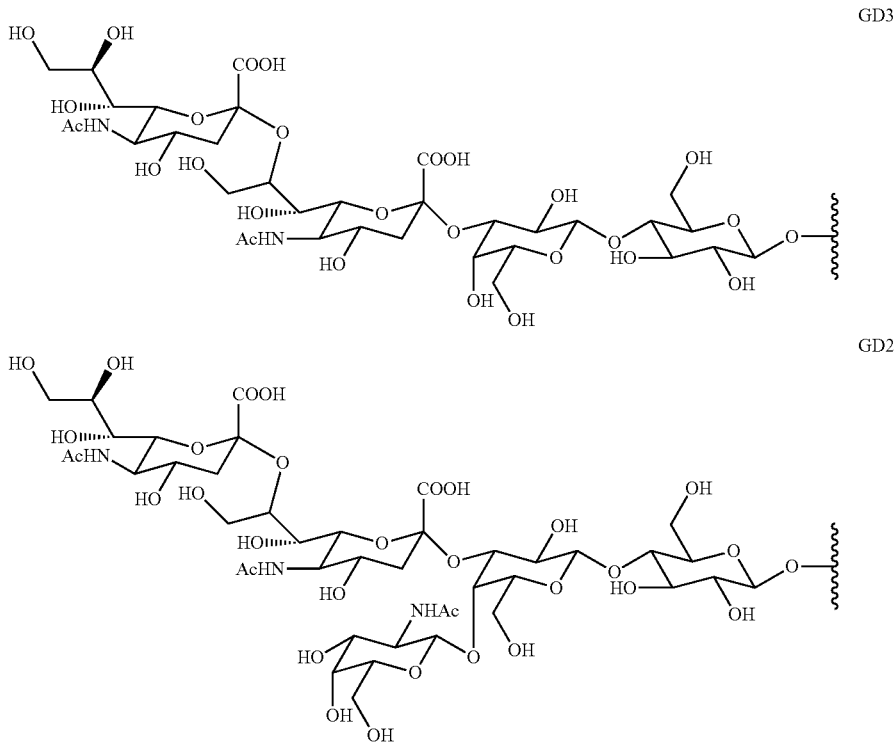

The term "aryl", as used herein, is understood as referring to 6 to 10 membered aromatic groups, for example phenyl or naphthyl, preferably a phenyl. The aromatic ring can be substituted at one or more ring positions, preferably no substituent is present, and the amino group is preferably in a para position of a phenyl relative to the sugar moiety. Preferably, the "-aryl-$NH_2$" is therefore a 4-aminophenyl.

In one embodiment, the carbohydrate ganglioside analogue is an analogue of at least one of GD2, GD3, GM2 and GT1 b.

In one embodiment, the carbohydrate ganglioside analogue or the ganglioside carbohydrate multimer comprises at least one GD2 carbohydrate ganglioside analogue, or at least one GD3 carbohydrate ganglioside analogue.

In one embodiment, the carbohydrate ganglioside analogue or the ganglioside carbohydrate multimer is a tetramer of the carbohydrate ganglioside analogues. In one embodiment, the carbohydrate ganglioside analogue or the ganglioside carbohydrate multimer is useful for preventing or treating cancer. In one embodiment, the carbohydrate ganglioside analogue or the ganglioside carbohydrate multimer is useful for treating cancer. In one embodiment, the cancer is a ganglioside-positive cancer. In another embodiment, the cancer is a neuroblastoma, a melanoma, or a glioma. In one embodiment, the cancer is breast cancer or small cell lung cancer.

In one embodiment, there is provided an antibody specifically binding to the carbohydrate ganglioside analogue or the ganglioside carbohydrate multimer as defined herein. In one embodiment, the antibody is a monoclonal antibody, a polyclonal antibody or a humanized antibody. In one embodiment, the antibody is for preventing or treating cancer. In one embodiment, the cancer is a ganglioside-positive cancer. In one embodiment, the cancer is neuroblastoma, a melanoma, or a glioma. In one embodiment, the cancer is breast cancer or small cell lung cancer. In one embodiment, the cancer is breast cancer or small cell lung cancer.

In one embodiment, there is provided a vaccine comprising the carbohydrate ganglioside analogue or the ganglioside carbohydrate multimer as defined herein and a carrier. In one embodiment, the vaccine is for preventing or treating cancer. In one embodiment, the cancer is a ganglioside-positive cancer. In one embodiment, the cancer is neuroblastoma, a melanoma, or a glioma. In one embodiment, the cancer is breast cancer or small cell lung cancer.

In one embodiment, the carbohydrate ganglioside analogue or the ganglioside carbohydrate multimer for the methods or use defined herein is formulated for injection. In one embodiment, the vaccine is formulated for a transdermal administration or a parental administration. In one embodiment, the parental administration is an intramuscular administration, a subs-cutaneous administration or an intravenous administration In a particular embodiment, GD2 glycoconjugates that are immunogenic are disclosed herewith which are applied as anti-tumor vaccines.

It is disclosed herein the design and characterization of a water-soluble analog of GD2 and GD3 carbohydrate conjugated to form a dendrimeric (e.g. tetrameric, hereafter "tetra-GD2" or "tetra-GD3").

Tetrameric gangliosides carbohydrate conserves the native structural features of naturally occurring GD2 or GD3 for example, but are immunogenic and elicits cytotoxic anti-gangliosides humoral and cellular responses in vivo. Tetra-GD2 for example is effective as a GD2-cancer vaccine in prophylactic and in therapeutic paradigms. It is provided an effective anti-tumor vaccine, targeting cell surface carbohydrates, that rapidly elicits humoral and cellular immune responses that are protective in therapeutic paradigms.

Gangliosides accumulate on the outer leaflet of cell membranes, with the ceramide and lipids embedded and the carbohydrate head exposed. This should enable recognition by the immune system because complex gangliosides are neo-antigens and are defined as tumor markers. In addition, even antigenic gangliosides are poor immunogens. The immune system may recognize a carbohydrate as "self" without mounting a response or it may generate cross-reactive pathological responses (e.g. Guillain-Barré syndrome is due to an anti-GM1 antibody).

A synthetic carbohydrate analog of GD2 and GD3 that is immunogenic, and which can be used to generate selective immunity against tumors was generated.

It is believed that the analog of G (such as an analogue of at least one of GD2, GD3, GM2 and GT1b) can be multimeric, i.e. a dimeric, trimeric, tetrameric or any other form suitable for allowing a proper spatial positioning.

It is believed, in particular that the analog of GD2 and GD3 can be multimeric, i.e. a dimeric, trimeric, tetrameric or any other form suitable for allowing a proper spatial positioning of GD2 or GD3. Encompassed herein is a multimer of 2, 3, 4, 5, 6, 7, 8, 9, 10, 11, 12, 13, 14, 15 or 16 of the carbohydrate ganglioside analogue as described herein.

Scheme 1 below illustrates an immunogenic synthetic carbohydrate analog of GD2 and GD3 in a tetrameric form.

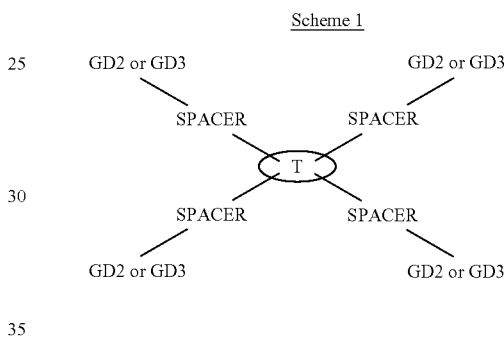

Scheme 1

The analog essentially comprises a central multimeric (or as shown above tetrameric) core allowing to covalently bond a spacer which in turn is also covalently bound to the desired GD2 or GD3. A typical example of such spacer is —(C=X)—, wherein X is N or X (such as —(C=S)— or —(C=O)—). The spacer can be introduced by the use of the isocyanate or isothiocyanate chemistry. FIG. 1c demonstrate a specific example, however the chemistry would be applicable to GD2/GD3-aminoaryl compounds disclosed above.

Preferably, the central core comprises an ethylene diamine residue on which is attached a multiplicity of terminal (i.e. primary) amino groups as generally described in scheme 2

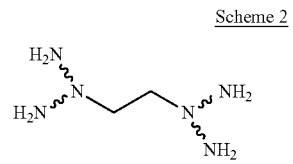

Scheme 2

An example of such core can be a PAMAM compound, a number of which are commercially available (see Aldrich Catalog at www.sigmaaldrich.com). Preferably, the central multimeric core has a multiplicity of terminal (i.e. primary) amino groups. Examples of PAMAM compounds include generation 0.0 PAMAM

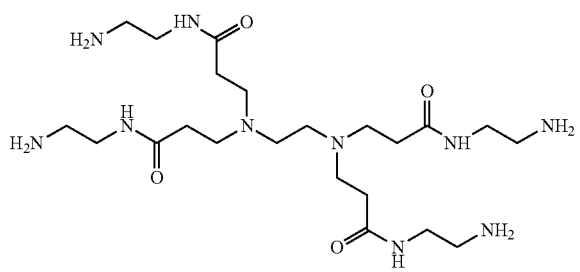 [SMILES: NCCNC(=O)CCN(CCC(=O)NCCN)CCN(CCC(=O)NCCN)CCC(=O)NCCN]

Higher generations of PAMAM compounds include PAMAM on which the terminal —NH₂ are further (partially or completely) functionalized with residues:

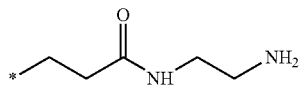 [SMILES: *CCC(=O)NCCN]

A partial representation of such higher generation PAMAM is as follows:

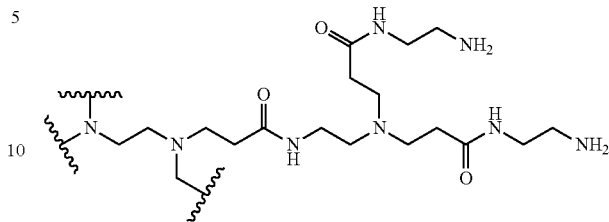

wherein the remaining "arms" (showing a wavy line) can also optionally have amidoamine residues to provide multimer of up to 8 that can further be expanded.

An example of immunogenic synthetic carbohydrate analog of G (such as GD2 and GD3) in a tetrameric when the central core is a generation 0.0 as displayed above can be illustrated by the following

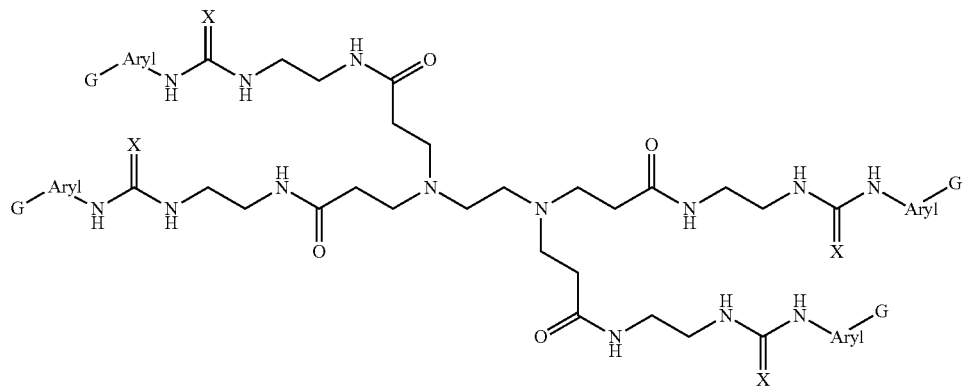

wherein G is as defined above, or preferably

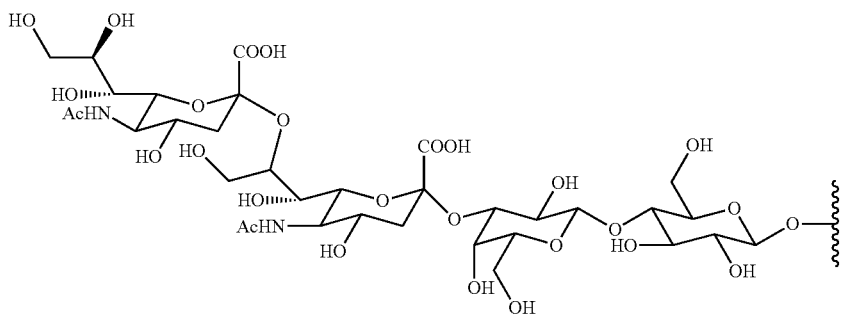

-continued

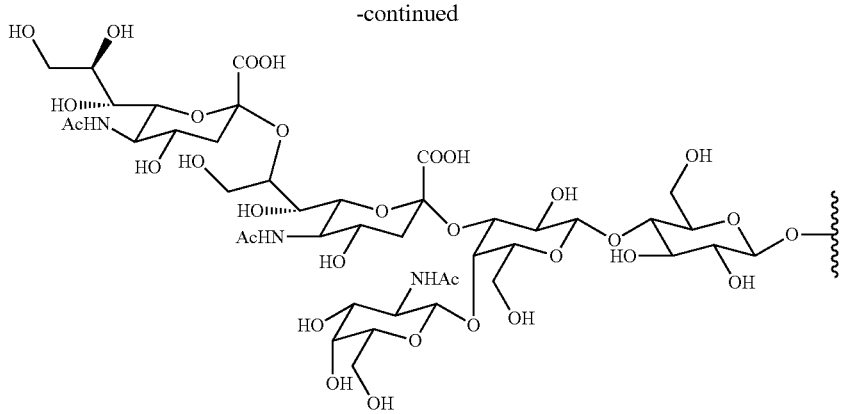

X is O or S, preferably X is S.

GD2 or GD3 derivatives can be synthesized as described in Gilbert et al., 2002, J Biol Chem, 277: 327, while modifying the process of Tong et al., 2010, Chem Biol, 17: 183 to use a suitably functionalized β-D-lactopyranoside bearing an amino group that can be used to covalently bond GD2 or GD3 to the central multimeric core. For example, the functionalized β-D-lactopyranoside can be a C1-β-D-lactopyranoside amino aryl derivative, or preferably an aminophenyl-β-D-lactopyranoside or more preferably a β-aminophenyl-β-D-lactopyranoside.

The functionalized β-D-lactopyranoside can be further derivatized so that the central multimeric (or as shown above tetrameric) core can be covalently bound. The functionalized β-D-lactopyranoside can be reacted with a suitable reagent to provide an activated carbonyl residue. For example, the C1-amino aryl derivative, or preferably an aminophenyl-β-D-lactopyranoside or more preferably a β-aminophenyl-β-D-lactopyranoside can be reacted with phosgene, diphosgene, triphosgene, thiophosgene, carbonyl dimidazole, disuccinimidyl carbonate, or other suitable reagent to provide the corresponding isocyanato, isothiocyanato, carbonylimidazolyl or succinimidyl carbonyl derivative.

The central multimeric core can then be reacted with the functionalized β-D-lactopyranoside having the activated carbonyl residue described above to provide the desired immunogenic molecule.

As an alternative synthetic approach, the central multimeric core (such as PAMAM) can be first reacted with a suitable reagent to provide an activated carbonyl residue as described above. Then the functionalized β-D-lactopyranoside comprising an amino group can be added to provide the desired immunogenic molecule.

It will be clear to a person of ordinary skill that if a further additional therapeutic agent is required or desired, ratios will be readily adjusted. It will be understood that the scope of combinations described herein is not particularly limited, but includes in principles any therapeutic agent useful for the prevention and treatment of cancer.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician.

The desired dose may conveniently be presented in a single dose or as divided dose administered at appropriate intervals, for example as two, three, four or more doses per day.

Pharmaceutical compositions include, without limitation, those suitable for transdermal, or parenteral (including intramuscular, sub-cutaneous and intravenous) administration.

The methods for preparing a pharmaceutical composition can include the steps of bringing into association the compound as defined herein and pharmaceutically acceptable excipients.

The compounds and combinations as defined herein may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilisation from solution, for constitution with a suitable vehicle, e.g. sterile water or saline, before use.

A specific embodiment is described below, followed by examples.

Figure 1C:
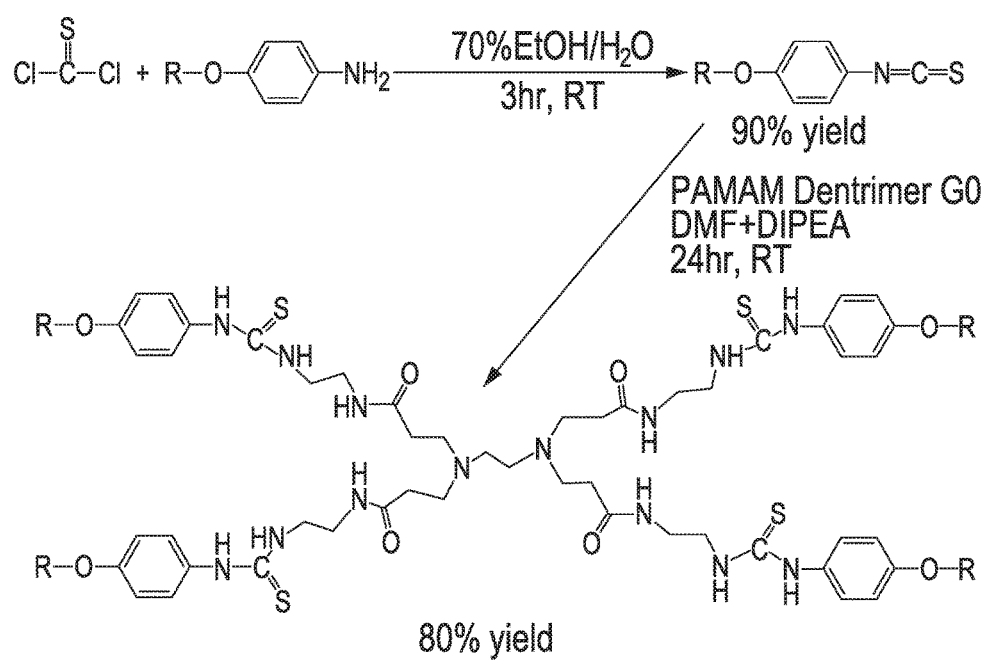
FIG. 1C illustrates a scheme for the synthesis of an antigen as disclosed herein.
Figure 2A:
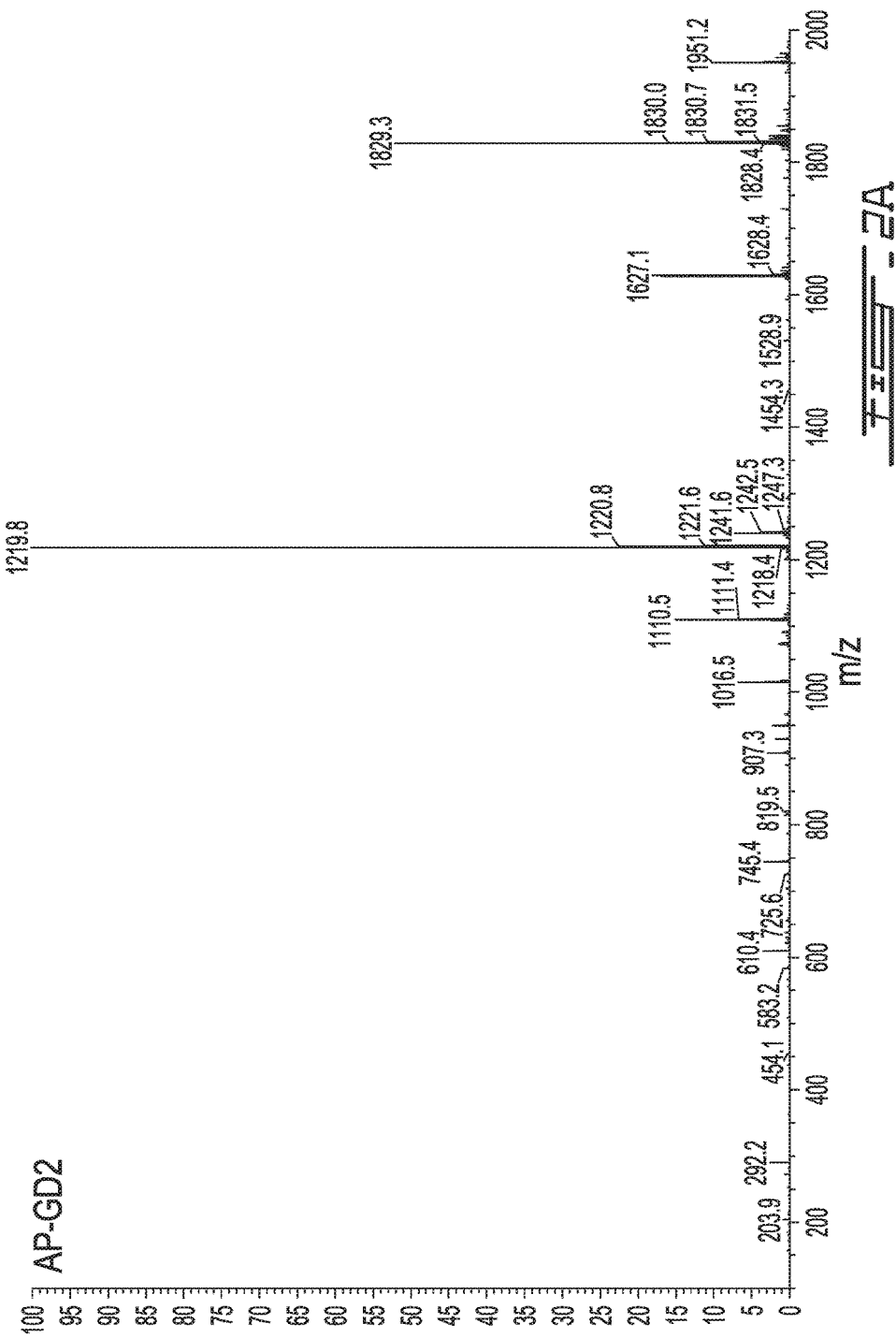
FIG. 2A illustrates a mass spectrum of amino phenyl ether-analog of GD2 (AP-GD2)
Figure 2B:
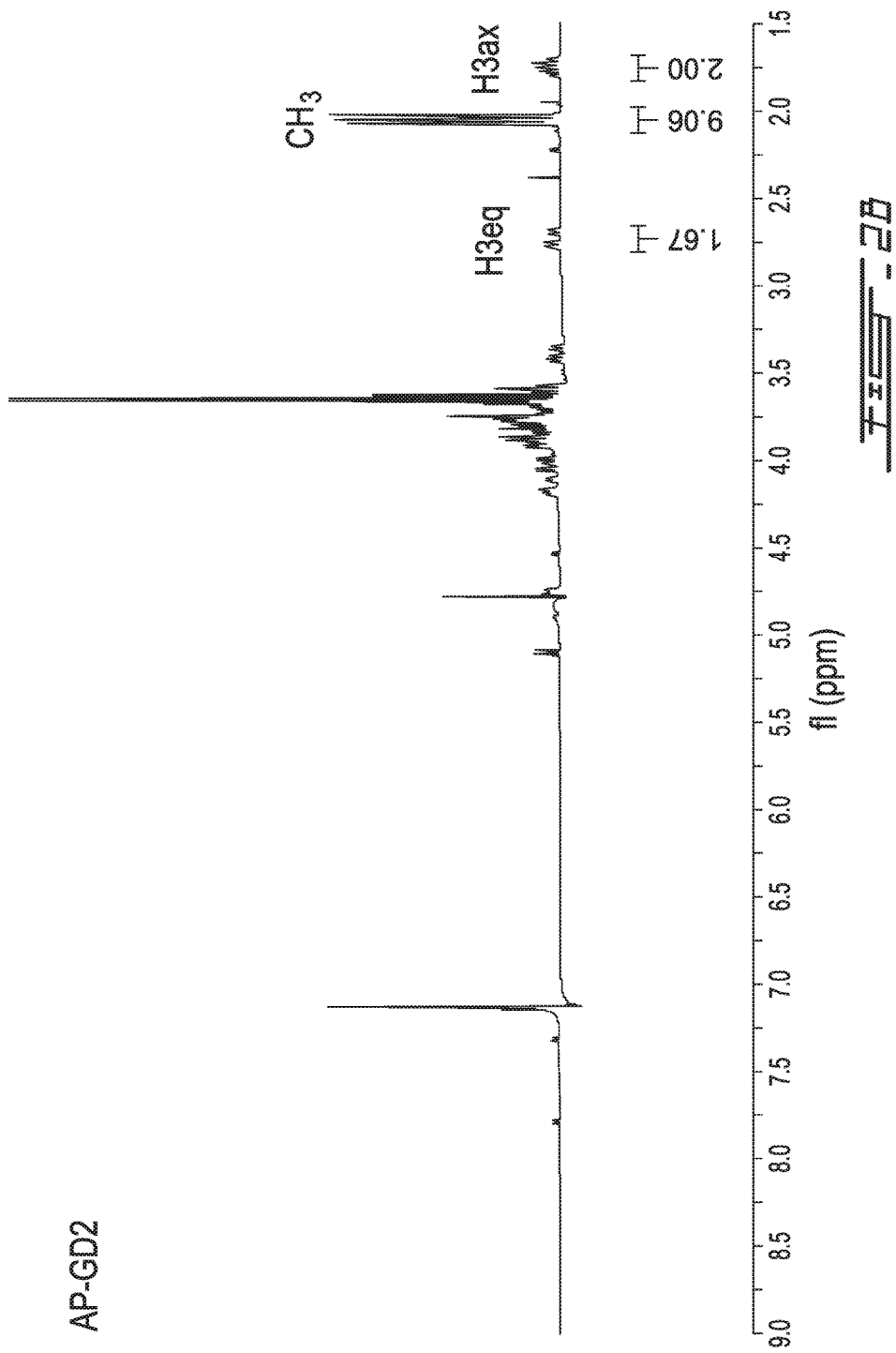
FIG. 2B illustrates a H-NMR spectrum of amino phenyl ether-analog of GD2

An amino phenyl ether-GD2 analog (herein AP-GD2), which has the correct GD2 carbohydrate structure but with an amino phenyl group replacing the ceramide and lipids is disclosed (see FIG. 1B). This analog is water-soluble. In AP-GD2, the bond between the phenyl group and the first sugar is preferably in the β-configuration, which is the configuration between ceramide and the first sugar in native gangliosides. This bond is critical for displaying a proper and homogeneous structure throughout the whole carbohydrate. The expected mass and configuration was verified by mass spectrometry (FIG. 2A), and NMR spectroscopy respectively (FIG. 2B).

Figure 2C:
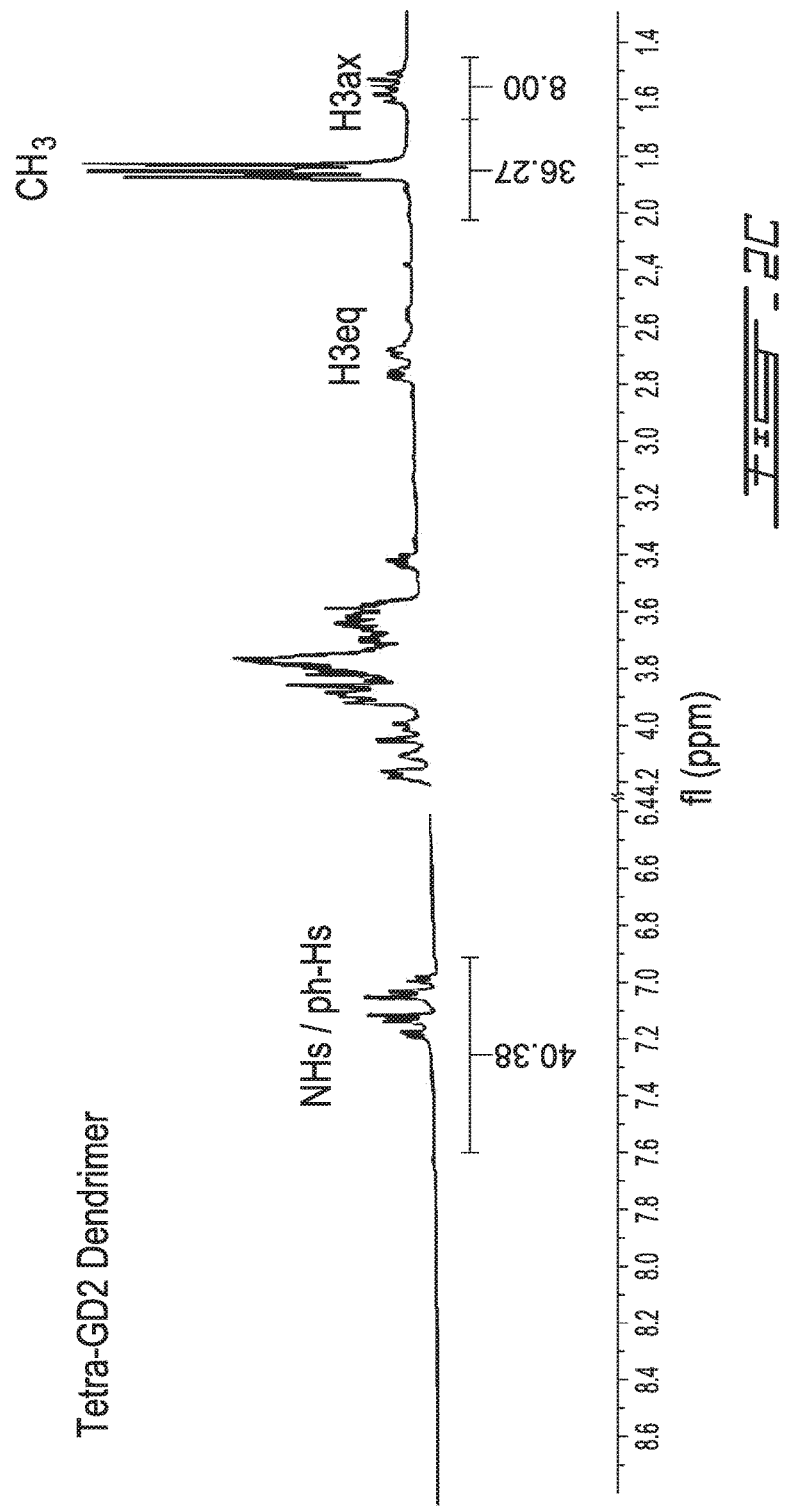
FIG. 2C illustrates a H-NMR spectrum of tetra-GD2 dendrimer in deuterated water.

AP-GD2 was converted to its corresponding isothiocyanatophenyl analog, and this intermediate was coupled to the terminal free amines of a tetravalent PAMAM G0 linker dendritic core (FIG. 1C). The formation of the thiourea-bridge between AP-GD2 and the PAMAM G0 linker was verified by a carbon chemical shift at 178 ppm that appears in the spectrum of HMBC (NHC(S) NHPh). The formation of the tetrameric product was verified by 1D-$^1$H-NMR. The 1D-$^1$H-NMR spectra showed a single signal pattern for all sugar units and indicated a 40:36:8 ratio of the amide NHs, NHC(S) NHPh, H-ortho, H-meta, NHAc/CH3/$H_{ax}$ or $H_{eq}$, demonstrating that the GD2 dendrimer is indeed tetravalent (FIG. 2C).

The tetra-GD2 antigen was designed to be used as an immunogen in tumor therapeutic studies. The rationale for the design of tetra-GD2 as a potential immunogen was based on the following concepts. First, presentation of tetra-GD2 may more closely mimic the oligomeric display of GD2 normally clustered in membrane rafts. Second, the sugar AP-GD2 analog can be easily conjugated to PAMAM linker at room temperature under mild conditions. Third, chemoenzymatic synthesis guarantees the appropriate configuration of the glycosidic linkages, thus maintaining the conformation of the whole carbohydrate. Fourth, the antigens would be homogeneous and well-characterized chemically. Fifth, the resulting product would be water soluble and stable. All of these features are desirable for a vaccine and can be translated to AP-GD3 disclosed herewith.

Mice were immunized up to four times with tetra-GD2. Sera were collected four days after each immunization, and samples were tested for the presence of anti-ganglioside antibodies. Immunization with tetra-GD2 generated high titer and selective antisera against tumor-marker GD2 and GD3 gangliosides in 22 out of 25 mice (88%).

Data from FACScan assays demonstrated that sera from immunized mice had antibodies that reacted selectively with cell surface GD2 and GD3 in tumor cells (see FIG. 3A and Table 1). Their sera contained antibodies of the IgG and IgM isotypes (based on the isotype-specific secondary reagents used). Sera bound to EL4-GD2$^+$ and/or EL4-GD3$^+$ cells. Negative control normal mouse serum pre-immune (NMS) had no reactivity. Positive control mAbs show that EL4-GD2$^+$ cells express GD2 but not GD3, and that EL4-GD3$^+$ cells express GD3 but not GD2. In cellular controls, the sera did not bind to Jurkat cells that do not express GD2 or GD3, but do express many other gangliosides such as GM1.

TABLE 1

Anti-ganglioside reactivities of sera from mice immunized with GD2 tetramer

| Mouse | FACScan on cells | | ELISA | |
|---|---|---|---|---|
| | EL4 GD2 | EL4 GD3 | Plated GD2 | Plated GD3 |
| M1 | ++++++++++ | ++++++++ | + | ++ |
| M2 | ++ | ++ | − | − |
| M3 | ++ | ++ | − | − |
| M4 | − | ++ | − | − |
| M5 | + | ++ | + | − |
| M6 | +++ | ++ | + | − |
| M7 | +++ | +++ | ++ | +++ |

Figure 3B:
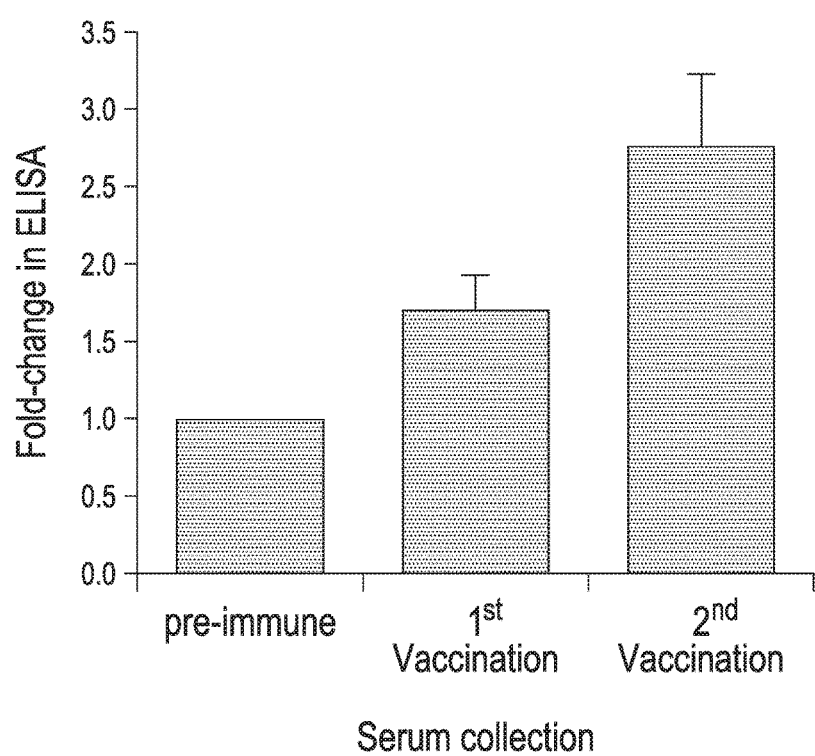
FIG. 3B illustrates serial dilutions of test or control sera studied using anti-mouse IgG secondary reagents.

Sera were also tested by ELISA for direct binding to immobilized gangliosides. Gangliosides GD2, GD3, or controls were immobilized on plates and the indicated dilutions of test and control pre-immune sera were assayed. Antibodies generated through vaccination bound selectively to GD2 (see FIG. 3B). One immunization was sufficient to elicit an increase in circulating anti-GD2 IgG, ~2-fold above background, and after a boost there was a ~3-fold increase above background (FIG. 3C). The antibodies also bound to GD3, but did not bind to GM1. Both anti-GD2 IgG and anti-GD2 IgM isotypes were detected. The IgG isotypes increased after each boost, suggesting B cell maturation and class switching (FIG. 3C). These ELISA data are consistent with the results obtained by FACScan.

Antibodies from mice vaccinated with tetra-GD2 killed EL4-GD2$^+$ cells in culture (FIG. 3D). EL4-GD2$^+$ cells were killed by immune serum in the absence of complement, an effect that has been reported for some anti-GD2 mAbs (Yoshida et al., 2001, Cancer Research, 61: 4244) (e.g. mAb 3F8 kills cell but mAb ME361 does not). In addition, killing of EL4-GD2$^+$ cells was confirmed by counting cells stained with the vital dye trypan blue, and by assessing their morphology.

Together, these data validate tetra-GD2 as an immunogen to generate and to mature a cytotoxic humoral immunity.

It has been demonstrated that glycopeptide vaccines could activate the adaptive immune system by binding to histocompatibility class II (MHC II) (Avci et al., 2011, Nature Medicine, 17: 1602). This suggested that T cell mediated immunity might also be activated by tetra-GD2. Consequently, primary T cells in a mixed lymphocyte reaction (MLR) measuring $^3$H-thymidine incorporation were tested. As target cells stimulators of T cell activation, mitomycin-treated EL4-GD2$^+$ were used, and Jurkat cells (GD2$^−$) were used as negative control (FIG. 4A). The EL4-GD2$^+$ or Jurkat cells treated with Mitomycin do not incorporate $^3$H-thymidine (188±4 cpm and 107±5 cpm respectively), hence they act only as stimulators.

T cells from mice vaccinated twice with tetra-GD2 proliferated robustly when challenged with EL4-GD2$^+$ cells, but they did not proliferate when challenged with Jurkat cells. In cellular controls, T cells from non-vaccinated mice did not proliferate when challenged with either EL4-GD2$^+$ or with Jurkat cells. In positive controls, treatment with ConA stimulated proliferation of T cells from control or vaccinated mice to a similar degree (21,457±504 cpm, and 19,834±309 cpm respectively). Similar data were obtained in related assays counting, by trypan blue exclusion, the number of proliferating T cells in each group (FIG. 4B). In these assays, 40,000 responding T cells from tetra-GD2 vaccinated mice were seeded with live cells Jurkat or EL4 as stimulators. After 7 days in vitro, all the EL4 target cells were dead, whereas Jurkat cells were alive and multiplying.

Together, these data validate tetra-GD2 as an immunogen to generate cellular immunity.

In a tumor-preventive paradigm, immunocompetent C57/Bl6 mice were immunized intraperitoneally twice at one-week intervals, followed by subcutaneous implantation of syngeneic EL4-GD2$^+$ cells, which are very aggressive and highly metastatic. EL4 cells are syngeneic and grow and metastasize very rapidly in these mice. Immunized mice (5≤n≤9) had primary tumors of significantly smaller size than control mice at all days measured (11, 14, 16 post tumor implantation) (FIG. 5A). The tumor-preventative vaccine experiments were reproduced independently three times (total n=22 immunized versus n=22 control mice). To compare all three independent experiments, the average tumor volumes of control mice for each experiment at day 16 were standardized to 100%. Using this criterion, overall the tumor volumes in the immunized mice were reduced by ~57% (FIG. 5B).

In a tumor-therapeutic paradigm, mice were first implanted with EL4-GD2$^+$ cells, and when tumors were visible/palpable, the mice were immunized two times with tetra-GD2 or control vehicle. In this more clinically relevant paradigm, immunized mice (4≤n≤6) had significantly delayed primary tumor growth compared to control mice, at all days measured (FIG. 5C). After 18 days all the control mice developed primary tumors averaging ~6,000 mm$^3$, and extensive lymph node metastasis. In contrast, the immunized mice had primary tumors ~2,300 mm$^3$.

The tumor-therapeutic vaccine data were reproduced in two independent experiments (N=13 immunized versus n=18 control mice). To compare all experiments, the average tumor volumes of control mice for each experiment at day 18 were standardized to 100%. Using this criterion, overall the tumor volume in the immunized mice were reduced by ~51% (FIG. 5D).

Mice bearing subcutaneous tumors received, by intraperitoneal injection, $4 \times 10^6$ T cells purified form tetra-GD2-immunized donor mice. The adoptively-transferred mice (n=6) had significantly delayed primary tumor growth compared to control untreated mice (n=6), at all days measured (FIG. 5E). After 14 days of tumor growth, the control groups developed primary tumors averaging ~1200 mm$^3$. In contrast, the adoptively transferred group had primary tumors ~500 mm$^3$.

Notably, the adoptively transferred group had no evidence of metastasis to the lymph nodes or the thymus, organs which are the major sites of metastasis observed for EL4 tumors. EL4 tumor metastasis causes enlargement of the tissue, and a corresponding increase in weight that can be quantified. Mice bearing tumors (n=6) have bigger lymph nodes than naïve mice not bearing tumors, the size is increased by ~10-fold. Mice bearing tumors (n=6) but receiving adoptive transfer of T cells had smaller lymph nodes, comparable to normal lymph nodes (FIG. 5F).

The T cells activated after vaccination were characterized further as to their CD4 and CD8 phenotype. T cells were isolated from tumor-bearing vaccinated mice or control mice, and the cells were cultured in dishes that had GD2 immobilized on the plastic. T cells from vaccinated mice proliferated robustly in GD2-coated dishes. In contrast, T cells from control mice did not proliferate on GD2-coated dishes. Although all mice are bearing tumors and are exposed to GD2, only the vaccinated mice can respond to this antigen. FACScan assays characterizing the cultures showed that the phenotype of the proliferating cells was predominantly CD8$^+$. The CD4/CD8 ratio in these cells changed due to the expansion of the CD8 subset, whereas the T cells from control mice retained the normal CD4/CD8 ratio (FIG. 6).

These data indicate that after vaccination activated T cells can respond to immobilized (multivalent) antigen in the absence of antigen presenting cells.

The presence of tumor-infiltrating lymphocytes was verified by immunostaining cryosections prepared from primary tumors. The EL4 tumors are "double negative" T cells, and do not stain with anti-CD4 or anti-CD8 antibodies. In mice that received adoptive transfer of T cells from immunized mice there was a significantly higher number of infiltrating CD8$^+$ cells in the primary tumors, compared to tumor-bearing mice that did not receive adoptive transfer. Anti-CD4 antibodies detected infiltrating CD4$^+$ cells in both groups.

Together, the data show that vaccination is sufficient to manage primary tumor growth and tumor metastasis in a realistic therapeutic paradigm, in which the vaccine is given after the tumor is established.

A novel tetravalent GD2 carbohydrate dendrimer has been developed as an effective carbohydrate immunogen, and as a therapeutic cancer vaccine. Biophysical characterization of the synthetic immunogen showed that it is a homogenous tetramer that maintains the desired β-linkages. Presentation of oligomeric carbohydrate structures to the immune system may stimulate more genuine and cytotoxic anti-tumor responses by mimicking the rafted GD2 in tumor membranes. In vivo and in vitro biological studies showed that the vaccine induces anti-GD2 cytotoxic antibodies and cytotoxic cellular immunity. Immunity elicited by the vaccine can delay the growth and the metastasis of an established tumor. In vivo studies disclosed herein confirm that the ganglioside vaccine can not only prevent tumor growth, but also suppress established tumor growth.

From the data generated for the tetravalent GD2 carbohydrate dendrimer described herein, the development of other cancer vaccines targeting carbohydrates, and that are adapted to other tumor-associated gangliosides such as GD3 are encompassed herein. A tetrameric GD3 carbohydrate, prepared from the amino phenyl ether-GD3 analog is disclosed herein (see FIG. 1B), similarly to AP-GD2, which conserves the native structural features of naturally occurring GD3, predictably is immunogenic and will elicit cytotoxic anti-gangliosides humoral and cellular responses in vivo.

Figure 7:
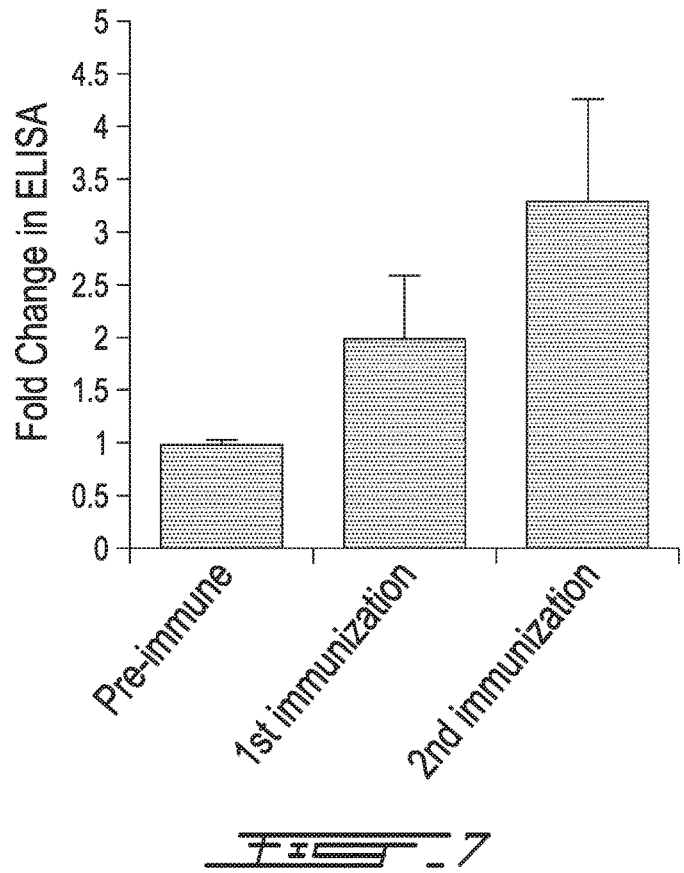
FIG. 7 is a representative ELISA data for sera showing anti-GD3-reactive antibodies of the IgG sub-class.

Using the same synthetic strategy as described for AP-GD2, a GD3 dendrimer (tetra-GD3) analog was generated and after two rounds of immunization, high titers of anti-GD3 antibodies were detected. As seen in FIG. 7, the humoral immunity elicited by vaccination with tetra-GD3 was detected.

The novel GD3 vaccine was evaluated as an anti-cancer agent in vivo and it was determined that immunized mice had primary tumors of significantly smaller size than control mice at all days measured (FIG. 8) and metastasis was virtually absent to the lymph nodes (FIG. 9) and to the lungs (FIG. 10). The GD3 vaccine reduces melanoma lung metastasis (FIG. 10). Accordingly, a novel tetravalent GD3 carbohydrate dendrimer has been developed as an effective carbohydrate immunogen, and as a therapeutic cancer vaccine.

The present disclosure will be more readily understood by referring to the following examples which are given to illustrate embodiments rather than to limit its scope.

Example I

Synthesis AP-GD2 and Tetra-GD2 Dendrimer

The carbohydrates were synthesized as described (Gilbert et al., 2002, J Biol Chem, 277: 327), by modification of the process for phenylthio-GD2 (Tong et al., 2010, Cehm Biol, 17: 183) in which the thio-phenyl analog originally reported was substituted with an p-aminophenyl-(β-D-lactopyranoside (AP-Lac), from Toronto Research Chemicals), for subsequent conjugation to the dendrimer (see below). AP-GD2 was water soluble (>20 mg/ml), and was purified to >99% purity by size-exclusion (Superdex 30 16 mm×85 cm column, GE Health Care). The measured molecular weight of AP-GD2 was 1218 g/mol and corresponded to expected values. Structures were verified by 1D and 2D NMR spectroscopy and mass spectrometry (EI-MS) (see FIGS. 2A and B). The chemoenzymatic synthesis of AP-GD2 had a final yield of ~90% pure material.

Thiophosgene (2 μl) was added to a stirred solution of AP-GD2 (2 mg) in 80% ethanol (300 μl), and the mixture was allowed to stand at room temperature for 3 h, when thin layer chromatography (ethyl acetate-methanol, 4:1) showed that all starting material had reacted and a single product had formed. Concentration almost to dryness gave a solid to which water was added. Filtration with washing of the product with water gave the isothiocyanatophenyl GD2 solution, which was freeze-dried to white powder (1.8 mg, 90% yield). The volatiles from a methanol solution of PAMAM GO (Dendritech, Inc) were evaporated under reduced pressure, and the resulting residue was dissolved in dimethylformamide (DMF). A solution of isothiocyanatophenyl GD2 (1.8 mg) in DMF (110 μl) was added drop-wise to a stirred DMF solution (100 μl) of N,N-diisopropylethylamine (0.5 μl) and PAMAM GO (2 μl of 0.854 μg/μl). The reaction was stirred at room temperature for 20 h, until no starting material was detected by TLC. The reaction mixture was diluted with 3 ml of water and dialyzed against water (MW cutoff 2 kDa, Spectrum Laboratories Inc.). The resulting solution was freeze-dried to give tetravalent PAMAM based GD2 as white powder in 80% yield (1.34 mg). The tetravalent PAMAM based GD2 was verified by 1D and 2D NMR spectroscopy. Mouse lymphoma EL4-GD2$^+$ (wild type EL4 cells) and Jurkat leukemia cells were obtained from ATCC. EL4-GD3$^+$ cells were developed by negative selection of EL4-GD2$^+$ with anti-GD2 mAbs, followed by limiting dilution sub-cloning. EL4-GD3$^+$ cells are stable and have the same in vitro growth properties and kinetics as EL4-GD2$^+$ cells. All cells were grown in RPMI 1640 medium (Wisent INC) supplemented with 5% fetal bovine serum, 2 mM glutamine, 10 mM Hepes and penicillin/streptomycin at 37° C. in 5% $CO_2$ humidified atmosphere. Flow cytometry showed that all cell lines express equal levels of cell surface GM1. Flow cytometry, and thin layer chromatography of ganglioside extracts, confirmed that EL4-GD2$^+$ cells express GD2 but not GD3, that EL4-GD3$^+$ cells express GD3 but not GD2, and that Jurkat cells do not express either GD2 or GD3.

Example II

In Vivo Characterization of Tetra-GD2

Immunization for FACS and ELISA Characterization of Sera

Tetra-GD2 (50 μg) in PBS was administrated intraperitoneally to C57/Bl6 mice. After 10 days, the mice were re-immunized intraperitoneally (25 μg)+subcutaneously (25 μg) in PBS. Four days later, blood samples were collected for analyses.

FACScan:

$2 \times 10^5$ cells of EL4-GD2$^+$, EL4-GD3$^+$, and Jurkat cells were washed with FACS buffer (PBS, 0.5% BSA, 0.05% NaN3), and incubated for 20 minutes on ice with 2 μl mouse antisera (1:50 dilution) or positive control anti-GD2 mAb (13 nM) or anti-GD3 mAb (13 nM). Cells were washed 2× with ice-cold FACS buffer, and incubated for 20 minutes on ice with FITC-conjugated anti-mouse IgG or FITC-conjugated anti-mouse IgM (Sigma). Cells were washed with FACS buffer, and freshly studied in a flow cytometer (Becton-Dickinson), and data were analyzed using CellQuest software. Mouse IgG or IgM and normal mouse sera were used as negative control antibodies. Jurkat cells were used as negative control cells.

Direct Binding ELISA:

Gangliosides (Advanced ImmunoChemical Inc.) were immobilized onto polystyrene Corning Strip Well 96-well plates (10 ng/well) (Fisher Scientific). The wells were then "blocked" with phosphate buffered saline containing 0.5% bovine serum albumin (PBS-0.5% BSA) for one hour. Wells were incubated for two hours with primary antibodies, including test sera, control pre-bleed mouse sera, mouse IgG (Sigma), or specific anti-ganglioside monoclonal antibodies. The plates were washed three times with PBS-0.5% BSA, followed by horseradish peroxidase (HRP)-conjugated anti-mouse antibody (Sigma) specific for mouse IgG isotypes, or mouse IgM isotype. After three washes with PBS-0.5% BSA and two with PBS, the colorimetric substrate TMB One Solution (Promega) was added, and the reaction was stopped with 0.5 N $H_2SO_4$. Plates were read at 450 nm (Benchmark Plus, Bio-Rad) (31).

Sera Isotyping:

Blood was collected after each round of immunization using a capillary blood collection system (Microvette, Sardstedt) and was centrifuged at 10000×g for 5 minutes at room temperature for serum separation. Isotyping of Ig present in serum was then performed using a mouse subisotyping kit (Calbiochem, cat#386445) following the manufacturer's specifications. Experiments were performed 4 times in triplicate for each serum.

Cytotoxicity Evaluated by MTT Assays

EL4-GD2$^+$ cells (5,000/well, in 96-well plates, Corning) were cultured in regular media supplemented with the indicated reagents. The survival/metabolic profile of the cells were quantified after 24 h using the tetrazolium salt reagent (MTT, Sigma) and UV absorption. Assays were done 5 times each in quadruplicate. Test reagents include positive control anti-GD2 mAbs (7 nM final concentration), negative control normal mouse IgG (7 nM final concentration). Sera collected from naïve mice (negative control), or from test mice vaccinated twice intraperitoneally. In these experiments vaccination was at days 3 and 10 and sera were collected at day 13. The times for serum collection followed the timelines of the tumor therapeutic paradigm (see below). The sera were semi-purified and ~50 μg/well of serum antibodies were applied. A small fraction of the serum antibodies would be anti-ganglioside antibodies, whereas the mAbs controls contain 100% anti-ganglioside IgG.

Mixed Lymphocyte Reaction (MLR) Evaluated by $^3$H-Thymidine Incorporation Assay EL4-GD2$^+$ cells and control Jurkat cells were treated with 25 μg/ml Mitomycin (Sigma) for 1 hr to arrest their proliferation. After the cells were washed three times with media to remove Mitomycin, they were plated in 96-well plates at $2 \times 10^5$ cells/well. Single cell suspensions of splenocytes were obtained from twice immunized (as above) and from vehicle injected control mice. Cells were separated following the protocol of the EASYSEP™ magnet (Stem Cell Tech). Similar amounts of T cells were obtained from each mouse spleen (>95% purity, data not shown). The T cells were plated at a ratio of 10:1 with Mitomycin-treated EL4 or Jurkat cells. As controls, cultures of T cells alone (no stimulating tumor cells) or T cells treated with ConcanavilinA were used. After 5 days of culture, 0.1μCi/well $^3$H-thymidine (Sigma-Aldrich) was added. DNA-incorporated $^3$H-thymidine was counted by liquid scintillation, and data are reported as average cpm±sd.

Example III

Tumor-Preventative Studies

Immunization for Tumor-Preventative Studies

C57BL/6 mice were vaccinated intraperitoneally four-times, each one week apart (50 μg each time). Control mice received only vehicle injections. One week after the fourth vaccination, $5 \times 10^5$ EL4-GD2$^+$ were injected subcutaneously. Ten days after tumor challenge, tumors were measured at the indicated times post-tumor implantation.

Immunization for Tumor-Therapeutic Studies $5 \times 10^5$ EL4-GD2$^+$ cells were injected subcutaneously in C57BL/6 mice, on the left flank. After three days, when the tumor was visible/palpable, mice were randomized and were vaccinated twice intraperitoneally on the right side, with either vehicle control or with tetra-GD2 dendrimer (50 μg in PBS). Tumors were measured at the indicated times post-tumor implantation.

Adoptive T Cell Transfer Therapeutic Studies

C57BL/6 mice were vaccinated intraperitoneally twice (one week apart) with 50 μg of tetra-GD2. Seven days after the second immunization, T cells from spleen and lymph nodes were isolated using the EasySep Negative Selection Mouse T Cell Enrichment Kit (Stemcell Technologies). Approximately $4 \times 10^6$ T cells were injected intraperitoneally to C57BL/6 mice that had been injected subcutaneously with $2.5 \times 10^5$ EL4-GD2$^+$ cells 3 days prior to the adoptive transfer. Tumors were measured at the indicated times and mice were euthanized 14 days post-tumor implantation in order to dissect the ipsilateral inguinal and axillary lymph nodes and assess metastasis.

Evaluation of Tumor Growth

The primary tumor was measured with a digital caliper, and data were analyzed by the following equation: V (mm$^3$)= 0.5×width×(length)$^2$. After euthanasia, mice were dissected and examined microscopically for evidence of metastasis to lymph nodes and thymus (organs to which EL4 cells are known to home).

Differences in tumor growth for the two groups were analyzed by two-tailed student t-tests; with significance at p<0.05 (*) and p<0.01 (**). Elsewhere, one-way ANOVA with Tukey-Kramer Multiple Comparisons Test compared the five different groups. A difference between results was considered significant at p<0.05 (*) and p<0.01 (**).

Example IV

In Vivo Characterization of Tetra-GD3

Safety. Vaccinated mice did not exhibit any signs of adverse effects that could be predicted from known side effects. All endpoints measured were negative, including those reported as problematic in clinical trials using other forms of GD2 or GD3 antigens (hyperalgesia, changes in behavior, mobility, and learning/memory). Hyper-immunized mice did not develop cross-reactive immunity to normal gangliosides, and there were no alterations to hematological profiles, liver or kidney enzyme profiles.

Using the same synthetic strategy as described in Example I, the GD3 dendrimer (tetra-GD3) analog was generated. After two rounds of immunization, high titers of anti-GD3 antibodies were detected, but not anti-GM1 Abs. Safety evaluation, as above, revealed no problems.

FIG. 7. Shows the humoral immunity elicited by vaccination with tetra-GD3. Representative ELISA data for sera showing anti-GD3-reactive antibodies of the IgG sub-class. Negative controls are normal mouse pre-vaccination serum and mouse Ig (Sigma). Binding is selective for GD3, whereas GM1 ELISA plates are negative (not shown). Data shown is n=8 individual samples averaged±sem.

The novel GD3 vaccine was evaluated as an anti-cancer agent in vivo. EL4-GD3+, expressing high levels of GD3 was used. In a preventative paradigm, mice were immunized twice prior to implantation of a very aggressive syngeneic EL4-GD3+. In a clinically relevant tumor-therapeutic model, adoptive transfer of T cells from vaccinated donor mice into mice bearing established subcutaneous tumors was performed. In both paradigms, immunized mice had primary tumors of significantly smaller size than control mice at all days measured (FIG. 8) and metastasis was virtually absent to the lymph nodes (FIG. 9) and to the lungs (FIG. 10).

Figure 8:
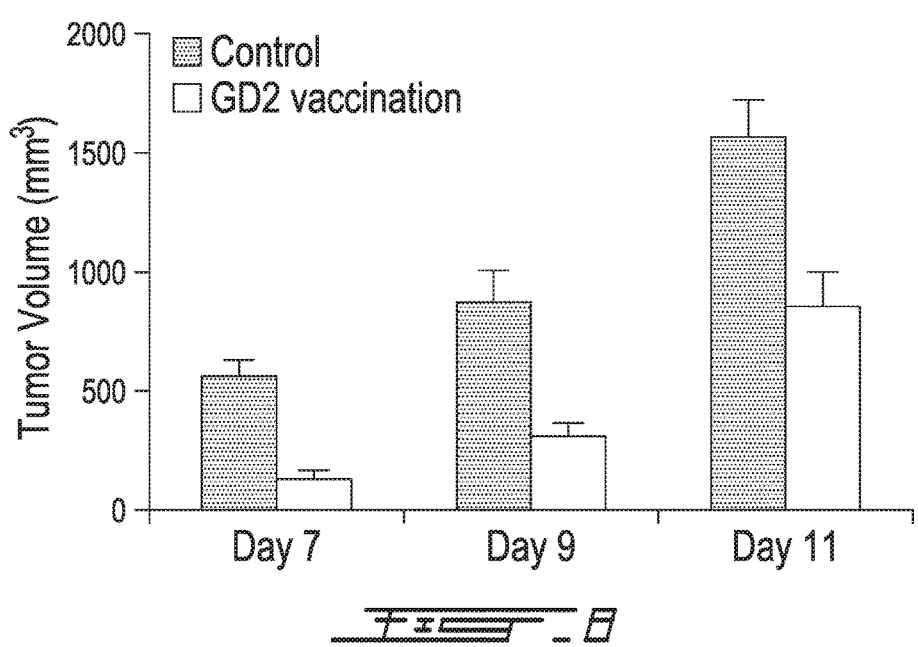

FIG. 8 illustrates the results of vaccination with tetra-GD3 protects against GD3+ tumor challenge. Mice were vaccinated intraperitoneally with tetra-GD3 (2×, 1 week apart, 10 ug/mouse each time, no adjuvant) before subcutaneous tumor implantation of EL4-GD3+ cells. Average primary tumor volumes±sd.

FIG. 9 represents the results of vaccination with tetra-GD3 protects against GD3+ tumor challenge. Mice were vaccinated intraperitoneally with tetra-GD3 (2×, 1 week apart, 10 ug/mouse each time, no adjuvant) before subcutaneous tumor implantation of EL4-GD3+ cells. Average lymph node volume±sd (indicative of metastasis, measured by detecting EL4 cells in the lymph node), n=8 each group. Lymph nodes are shown as an example.

FIG. 10 illustrates the observation that the GD3 vaccine reduces melanoma lung metastasis. 5×105 B16-GD3 melanoma cells were injected in the tail vein of C57BL/6 mice. After three days, mice were randomized and were vaccinated twice IP. Mice were sacrificed after 14 days. Lungs with dark spots of metastatic nodules were quantified (tumors contain melanin and can be easily seen).

While the invention has been described in connection with specific embodiments thereof, it will be understood that it is capable of further modifications and this application is intended to cover any variations, uses, or adaptations of the invention, as come within known or customary practice within the art to which the invention pertains and as may be applied to the essential features hereinbefore set forth, and as follows in the scope of the appended claims.

What is claimed is:

1. A ganglioside carbohydrate of formula

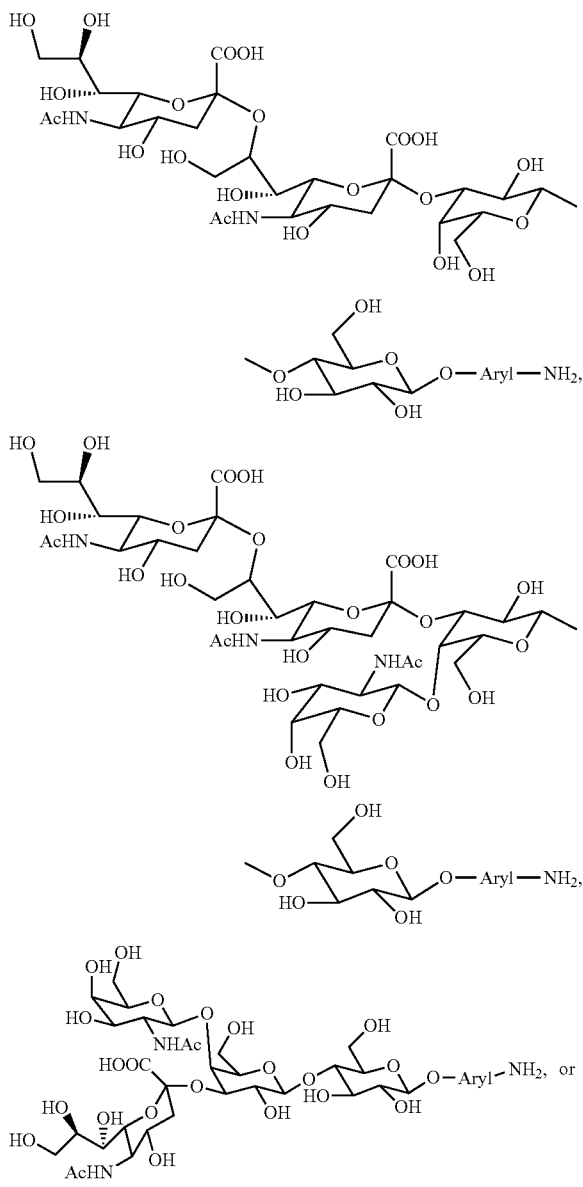

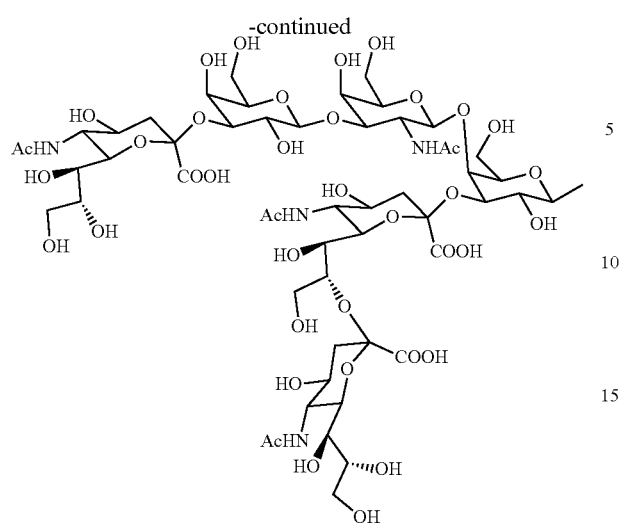
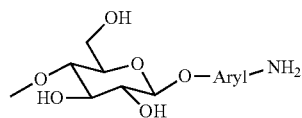
wherein Aryl is a C6 to C10 aryl, optionally substituted with an alkyl, aryl, or halogen substituent.
2. The ganglioside carbohydrate of claim 1 having the formula
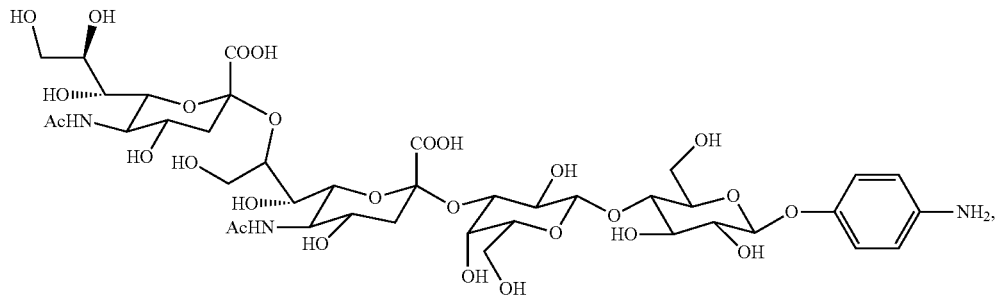
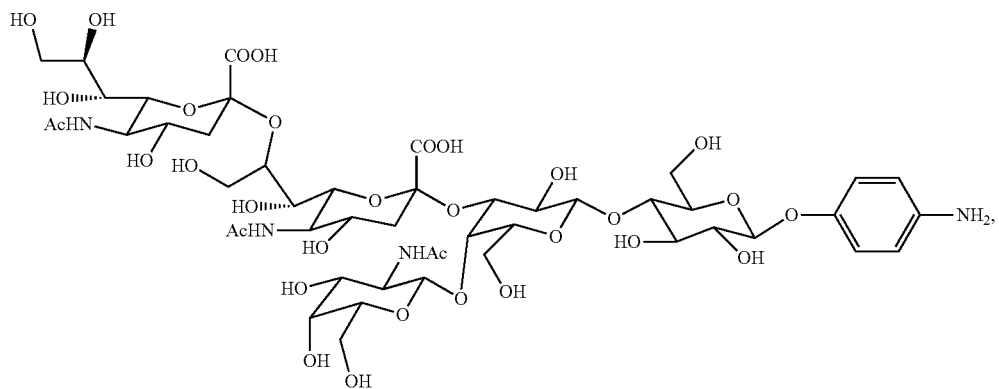
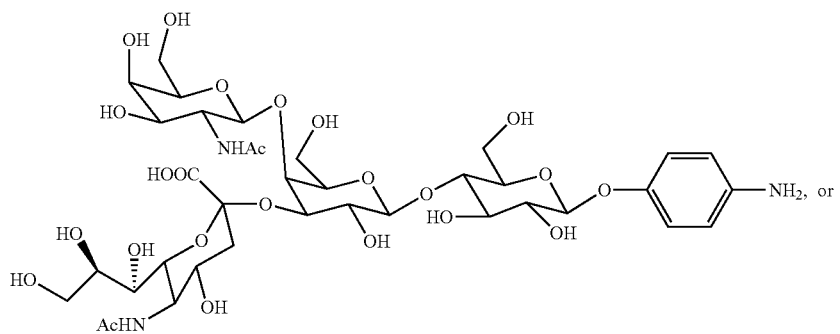

-continued

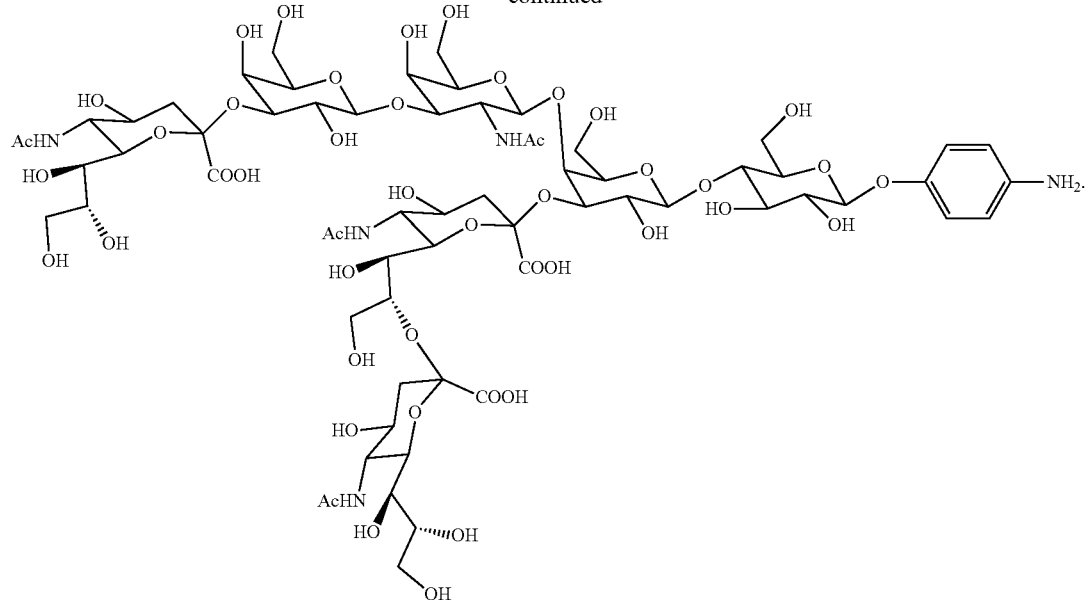

3. A ganglioside carbohydrate multimer comprising at least two ganglioside carbohydrates covalently bonded to a multimeric core molecule, wherein at least one of said ganglioside carbohydrates is a ganglioside carbohydrate of claim 1.

4. The ganglioside carbohydrate multimer of claim 3, wherein said ganglioside carbohydrate multimer comprises four ganglioside carbohydrates.

5. A ganglioside carbohydrate multimer having the formula

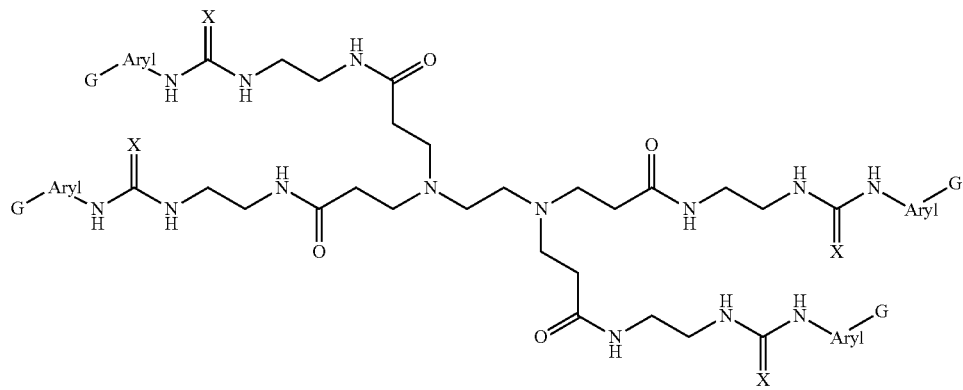

wherein Aryl is a C6 to C10 aryl, optionally substituted with an alkyl, aryl, or halogen substituent; X is O or S, and G is

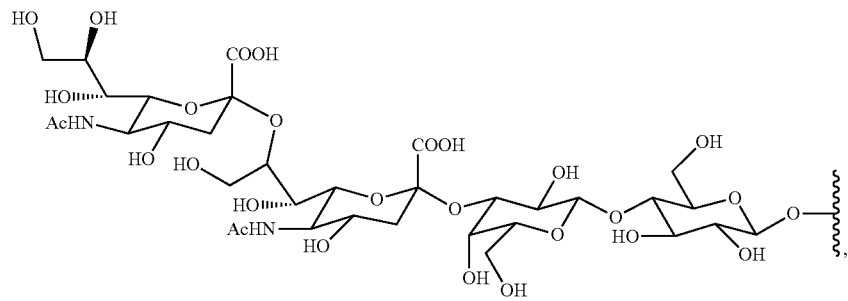

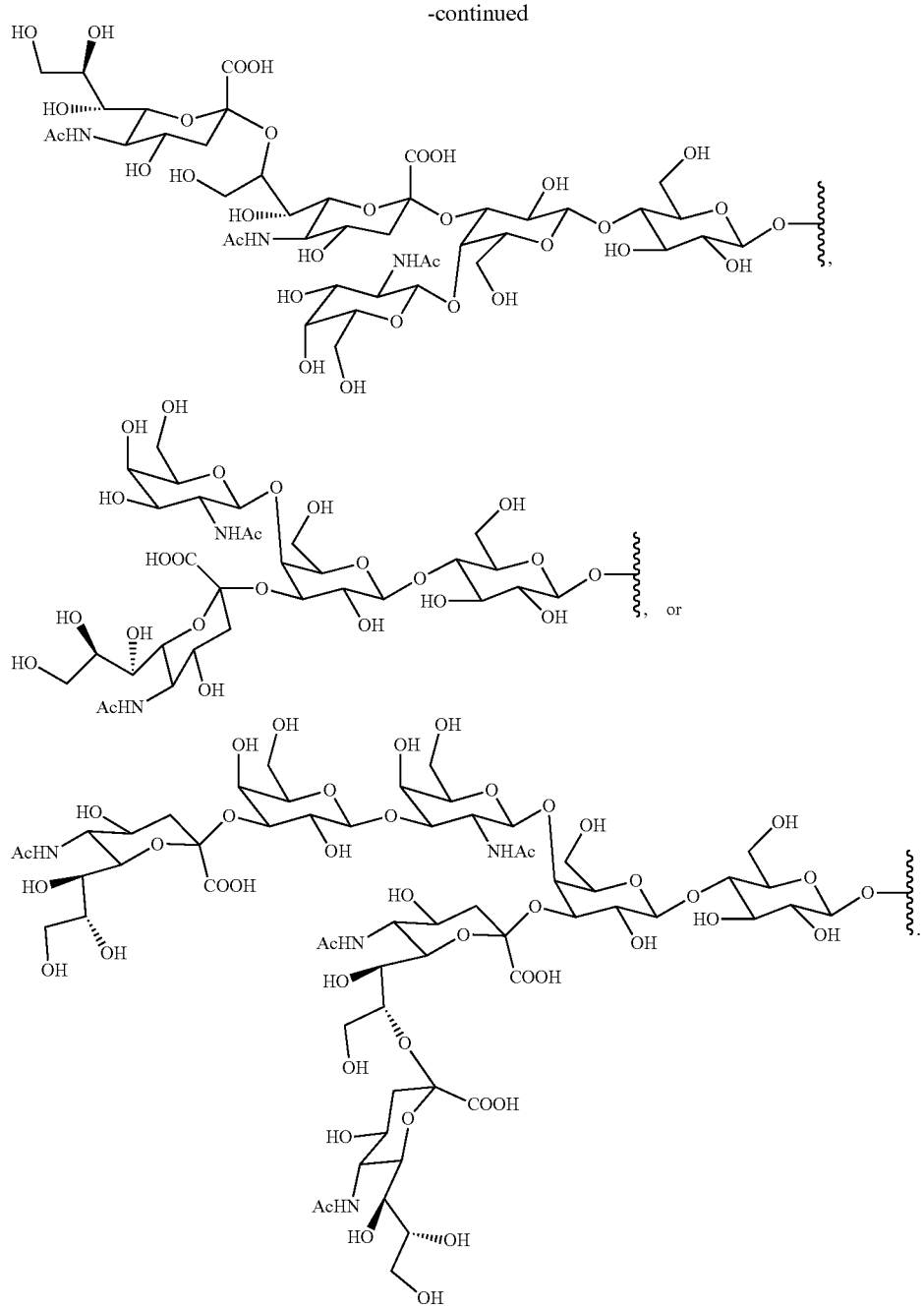

6. The ganglioside carbohydrate of claim 3, wherein said ganglioside carbohydrate is immunogenic against ganglioside-positive tumours.

7. The ganglioside carbohydrate of claim 3, for preventing or treating ganglioside-positive cancer.

8. The ganglioside carbohydrate multimer of claim 4, wherein said ganglioside carbohydrate multimer is immunogenic against ganglioside-positive tumours.

9. The ganglioside carbohydrate multimer of claim 4, for preventing or treating ganglioside-positive cancer.

10. The ganglioside carbohydrate multimer of claim 5, wherein said ganglioside carbohydrate multimer is immunogenic against ganglioside-positive tumours.

11. The ganglioside carbohydrate multimer of claim 5, for preventing or treating ganglioside-positive cancer.

* * * * *